(12) United States Patent
Toyoshima et al.

(10) Patent No.: US 9,982,238 B2
(45) Date of Patent: May 29, 2018

(54) METHOD FOR PRODUCING REGENERATIVE ORGAN PRIMORDIUM PROVIDED WITH GUIDE FOR TRANSPLANTATION, COMPOSITION CONTAINING REGENERATIVE ORGAN PRIMORDIUM PROVIDED WITH GUIDE FOR TRANSPLANTATION PRODUCED THEREBY, AND METHOD FOR TRANSPLANTING REGENERATIVE ORGAN PRIMORDIUM PROVIDED WITH GUIDE FOR TRANSPLANTATION

(75) Inventors: Koh-ei Toyoshima, Chiba (JP); Takashi Tsuji, Chiba (JP)

(73) Assignee: Organ Technologies, Inc., Tokyo (JP)

( * ) Notice: Subject to any disclaimer, the term of this patent is extended or adjusted under 35 U.S.C. 154(b) by 0 days. days.

(21) Appl. No.: 13/983,701

(22) PCT Filed: Jul. 7, 2011

(86) PCT No.: PCT/JP2011/067045
§ 371 (c)(1),
(2), (4) Date: Oct. 16, 2013

(87) PCT Pub. No.: WO2012/108069
PCT Pub. Date: Aug. 16, 2012

(65) Prior Publication Data
US 2014/0037592 A1 Feb. 6, 2014

(30) Foreign Application Priority Data
Feb. 9, 2011 (JP) .................. 2011-026614

(51) Int. Cl.
*A61K 35/12* (2015.01)
*C12N 5/071* (2010.01)
*A61L 27/38* (2006.01)

(52) U.S. Cl.
CPC ........ *C12N 5/0697* (2013.01); *A61L 27/3813* (2013.01); *A61L 27/3834* (2013.01); *A61L 27/3886* (2013.01); *C12N 5/0627* (2013.01); *C12N 5/0633* (2013.01); *A61K 35/12* (2013.01); *A61L 2430/18* (2013.01); *C12N 2502/13* (2013.01); *C12N 2502/1376* (2013.01); *C12N 2533/54* (2013.01)

(58) Field of Classification Search
USPC ....................................................... 424/93.7
See application file for complete search history.

(56) References Cited

U.S. PATENT DOCUMENTS

| 7,597,885 B2* | 10/2009 | Barrows | A61L 27/3847 424/93.7 |
| 2004/0172061 A1* | 9/2004 | Yoshioka et al. | 606/215 |
| 2010/0021866 A1* | 1/2010 | Tsuji et al. | 433/215 |
| 2010/0119997 A1 | 5/2010 | Tsuji et al. | |
| 2010/0129771 A1 | 5/2010 | Tsuji et al. | |
| 2011/0200559 A1* | 8/2011 | Koga | A61L 27/3843 424/93.1 |

FOREIGN PATENT DOCUMENTS

| EP | 2 130 909 A1 | 12/2009 |
| EP | 2130910 A1 | 12/2009 |
| JP | 2008-029756 A | 2/2008 |
| JP | 2008-029757 A | 2/2008 |
| JP | 2008-200033 A | 9/2008 |
| JP | 2008-206500 A | 9/2008 |
| WO | 2005/014774 A1 | 2/2005 |
| WO | 2006/129672 A1 | 12/2006 |
| WO | 2008/090826 A1 | 7/2008 |
| WO | 2008/105499 A1 | 9/2008 |

OTHER PUBLICATIONS

Chu et al. Newly made antibacterial braided nylon sutures. I. In vitro qualitative and in vivo preliminary biocompatibility study. Journal of Biomedical Materials Research. 1987;21:1281-1300.*
Ohyama M. Hair follicle bulge: a fascinating reservoir of epithelial stem cells. Journal of Dermatological Science. 2007;46:81-89.*
Matsuzaki et al. Role of hair papilla cells on induction and regeneration processes of hair follicles. Wound Repair Regen. 1998;6(6):524-30.*
Biazar et al. Types of neural guides and using nanotechnology for peripheral nerve reconstruction. International Journal of Nanomedicine. 2010;5:839-852.*
International Search Report in corresponding International Application No. PCT/JP2011/067045 dated Aug. 30, 2011 (7 pages).
W. Sonoyama et al., "Mesenchymal Stem Cell-Mediated Functional Tooth Regeneration in Swine"; PLoS One; vol. 1; e76; Dec. 2006 (8 pages).
English translation of an International Preliminary Report on Patentability with Written Opinion dated Aug. 13, 2013, issued by the International Bureau of WIPO, in related International Patent Application No. PCT/JP2011/067045 (11 pages).
Toyoshima, Koei, et al., "Kikan Genki-ho ni yoru Mohatsu no Saisei I Sai Kosei Moho Genki no Hinai Ishoku ni yoru Mohatsu Saisei"; Regenerative Medicine, vol. 10, suppl., Abstract 2P-141; issued Feb. 1, 2011, JST received date Feb. 14, 2011. (1 page).

(Continued)

*Primary Examiner* — Lynn Y Fan
(74) *Attorney, Agent, or Firm* — Osha Liang LLP

(57) ABSTRACT

A method for producing a regenerative organ germ for transplantation includes using regenerative organ germ for transplantation ensuring continuity with a recipient after transplantation and facilitating transplantation procedures. A method for producing a regenerative organ germ provided with a guide for transplantation includes preparing a regenerative organ germ by closely contacting a first cell mass, which substantially consists of mesenchymal cells, and a second cell mass, which substantially consists of epithelial cells, culturing these cell masses within a support, and inserting the guide into the regenerative organ germ.

14 Claims, 13 Drawing Sheets

(56) References Cited

OTHER PUBLICATIONS

Sharpe, Paul T., et al., Test-Tube Teeth; 2005 Scientific American, Inc., Aug. 2005. (8 pages).
Official Action dated Dec. 29, 2014, issued by the Taiwan Patent Office in related Taiwan Patent Application No. 100127028 (5 pages).
Chu, C. C., et al., "Newly made antibacterial braided nylon sutures. I. In vitro qualitative and in vivo preliminary biocompatibility study"; Journal of Biomedical Materials Research, vol. 21 (1987); pp. 1281-1300.
Ishida, Kentaro, et al., "The regulation of tooth morphogenesis is associated with epithelial cell proliferation and the expressionof Sonic hedgehog through epithelial-mesenchymal interations"; Biochemical and Biophysical Research Communications 405 (2011); Elsevier Inc.; doi: 10.1016/j.bbrc.2011.01.052; pp. 455-461.
Zoukbri, Driss, et al., "Mechanisms of Murine Lacrimal Gland Repair after Experimentally Induced Inflammation"; Investigative Ophthalmology & Visual Science, vol. 49, No. 10, Oct. 2008; pp. 4399-4406.
Ohyama, M., "Hair follicle bulge: a fascinating reservoir of epithelial stem cells"; Journal of Dermatological Science, vol. 46; 2007; pp. 81-89.
Matsuzaki, T., et al., "Role of hair papilla cells on induction and regeneration processes of hair follicles"; Wound Repair Regen., Nov.-Dec. 1998; 6(6): 524-30.
Extended European Search Report dated Dec. 17, 2014, issued by the European Patent Office, Munich, Germany, in corresponding European Patent Application No. 11858349.1 (8 pages).
Nakao, Kazuhisa, et al., "The development of a bioengineered organ germ method"; Nature Methods, vol. 4, No. 3, Mar. 2007; ISSN: 1548-7091, DOI: 10.1038/nmeth1012; XP055157475; pp. 227-230.
Narita, Atsushi, et al., "Effect of gelatin hydrogel incorporating fibroblast growth factor 2 on human meniscal cells in an organ culture model"; The Knee, vol. 16, No. 4, Aug. 1, 2009; XP026161412, ISSN: 0968-0160, DOI: 10.1016/J.KNEE.2008.12.011; pp. 285-289.
Enomoto, MD PhD, Soichiro, et al., "Long-term patency of small-diameter vascular graft made from fibroin, a silk-based biodegradable material"; Journal of Vascular Surgery, vol. 51, No. 1, Jan. 1, 2010; XP026818699, ISSN: 0741-5214; pp. 155-164.
Asakawa, Kyosuke, et al., "Hiar organ regeneration via the bioengineered hair follicular unit transplantation"; Scientific Reports, vol. 2: 424, May 28, 2012; XP055157502, DOI: 10.1038/srep00424; pp. 1-7.
Ogawa, Miho, et al., "Functional salivary gland regeneration by transplantation of a bioengineered organ germ"; Nature Communications, vol. 4: 2498, Oct. 1, 2013; XP055157506, DOI: 10.1038/ncomms3498; pp. 1-10.
Hirayama, Masatoshi, et al., "Functional lacrimal gland regeneration by transplantation of a bioengineered organ germ"; Nature Communications, vol. 4:2497, Oct. 1, 2013; XP055157508, DOI: 10.0138/ncomms3497; pp. 1-10.
Office Action dated Jan. 9, 2018, issued by the Canadian Intellectual Property Office in corresponding Canadian Patent Application No. 2,826,063 (4 pages).

\* cited by examiner

[FIG. 1]
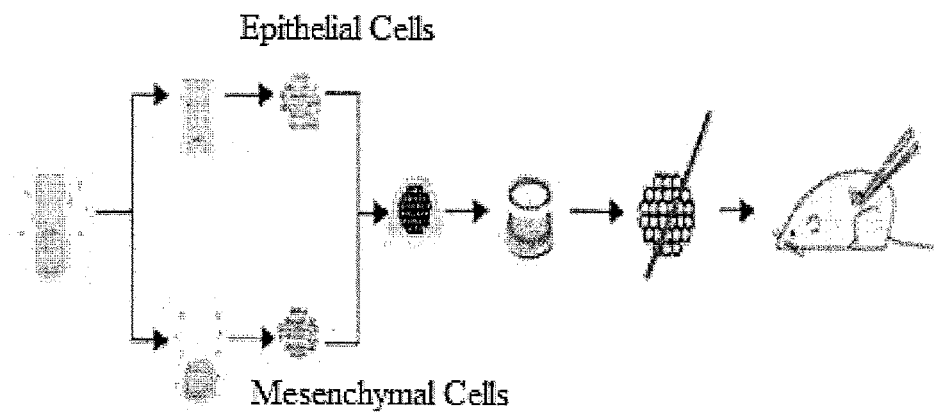
[FIG. 2]
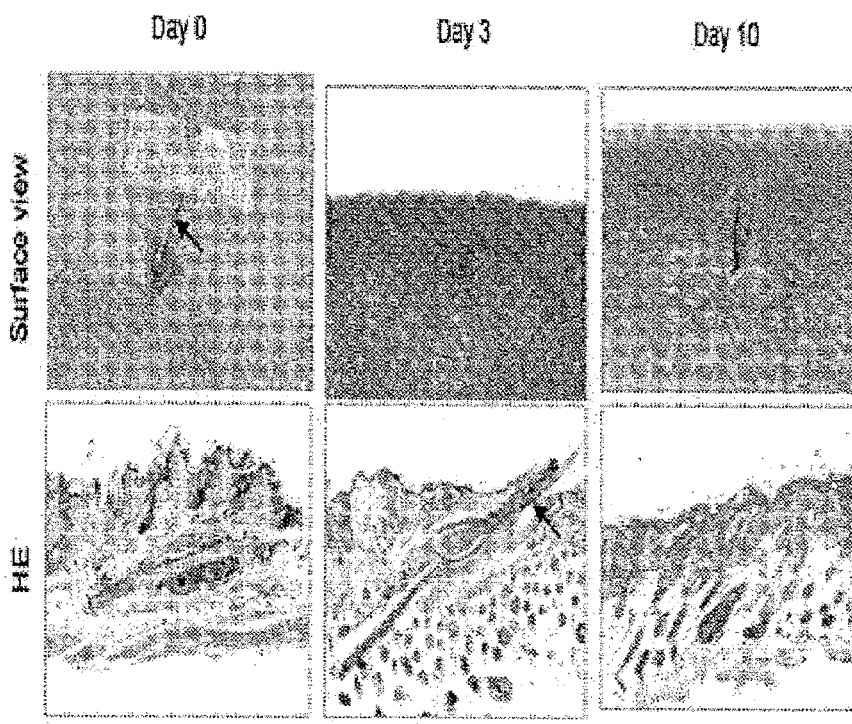

[FIG. 3]
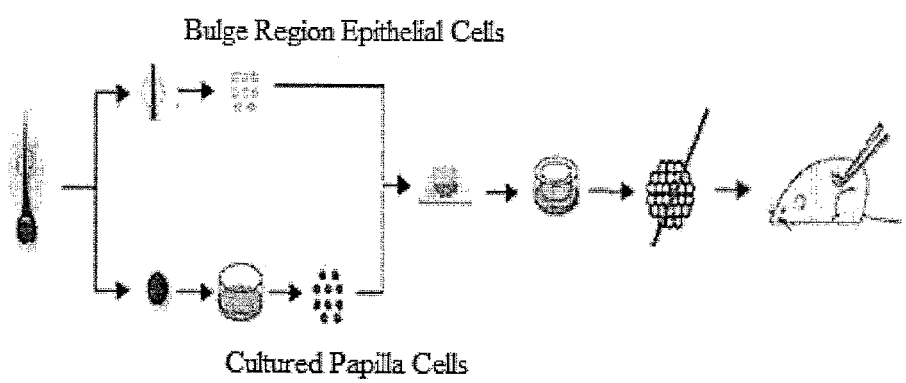
[FIG. 4]
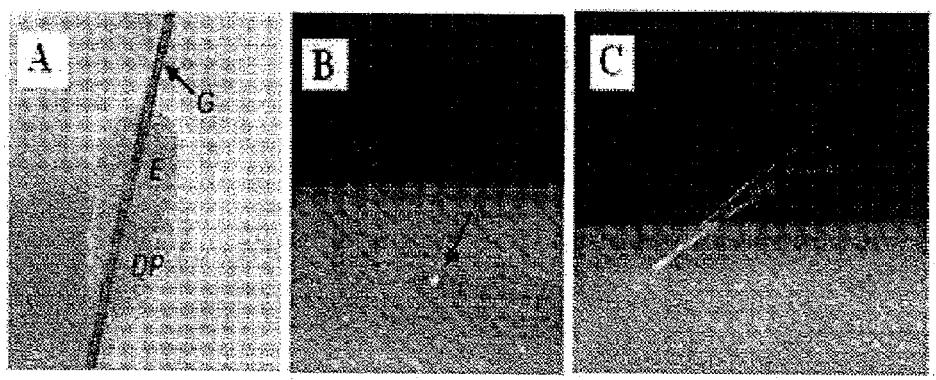

[FIG. 5]
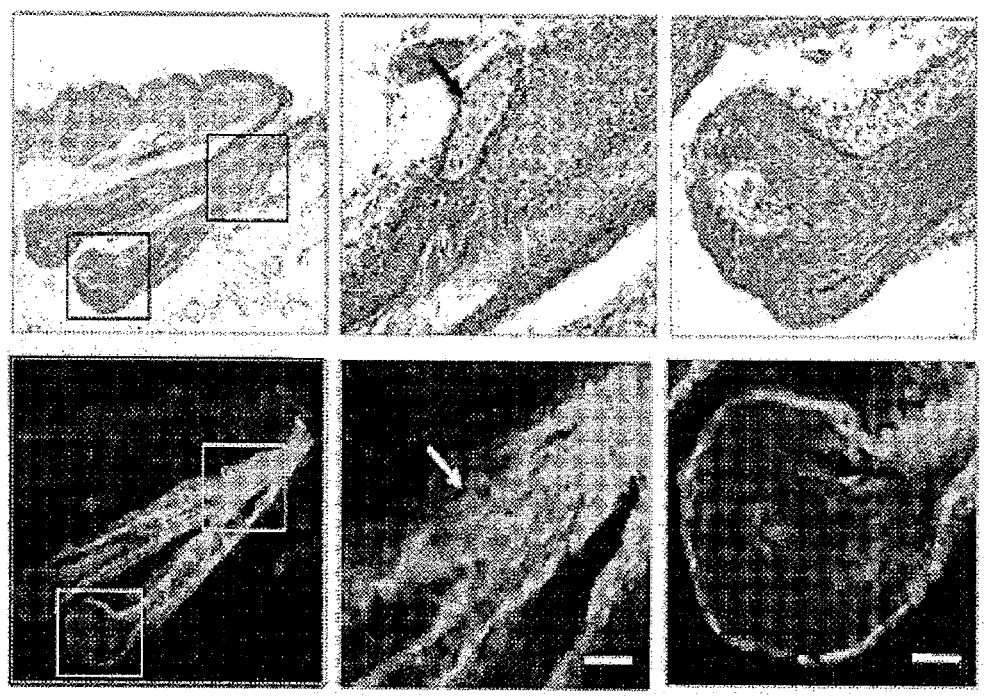
[FIG. 6]
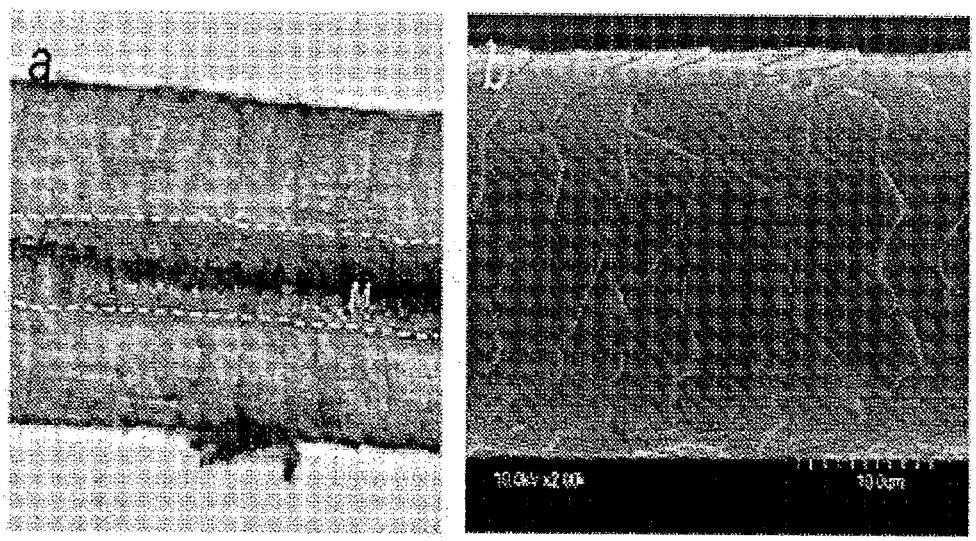

[FIG. 7]
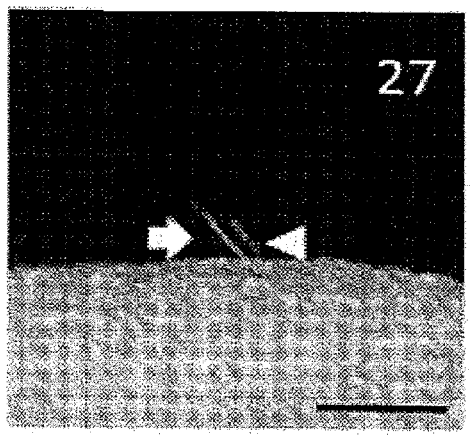
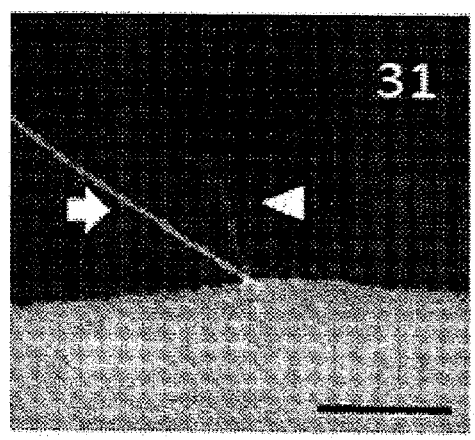
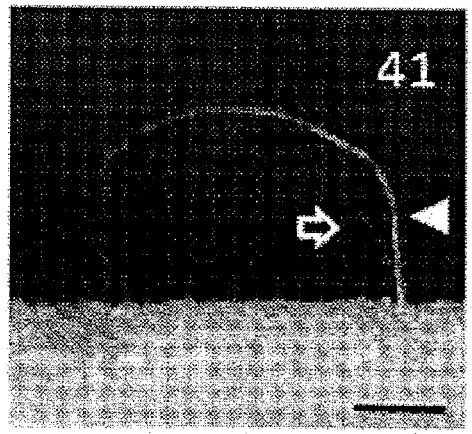
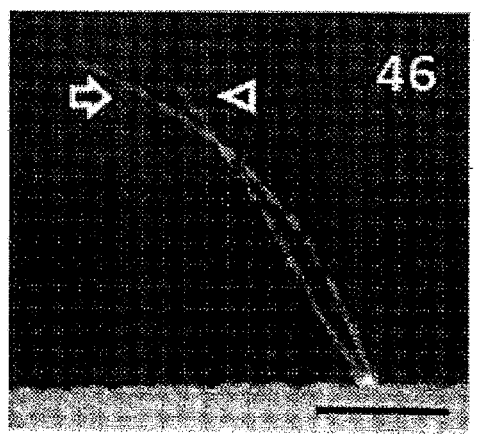

[FIG. 8]
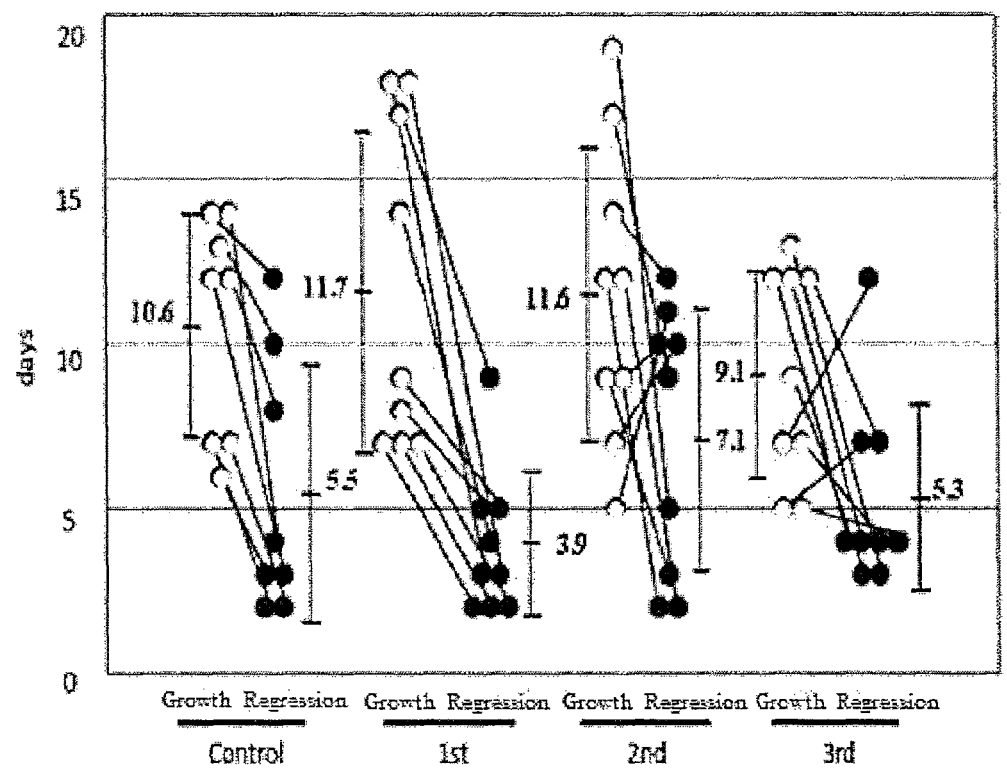

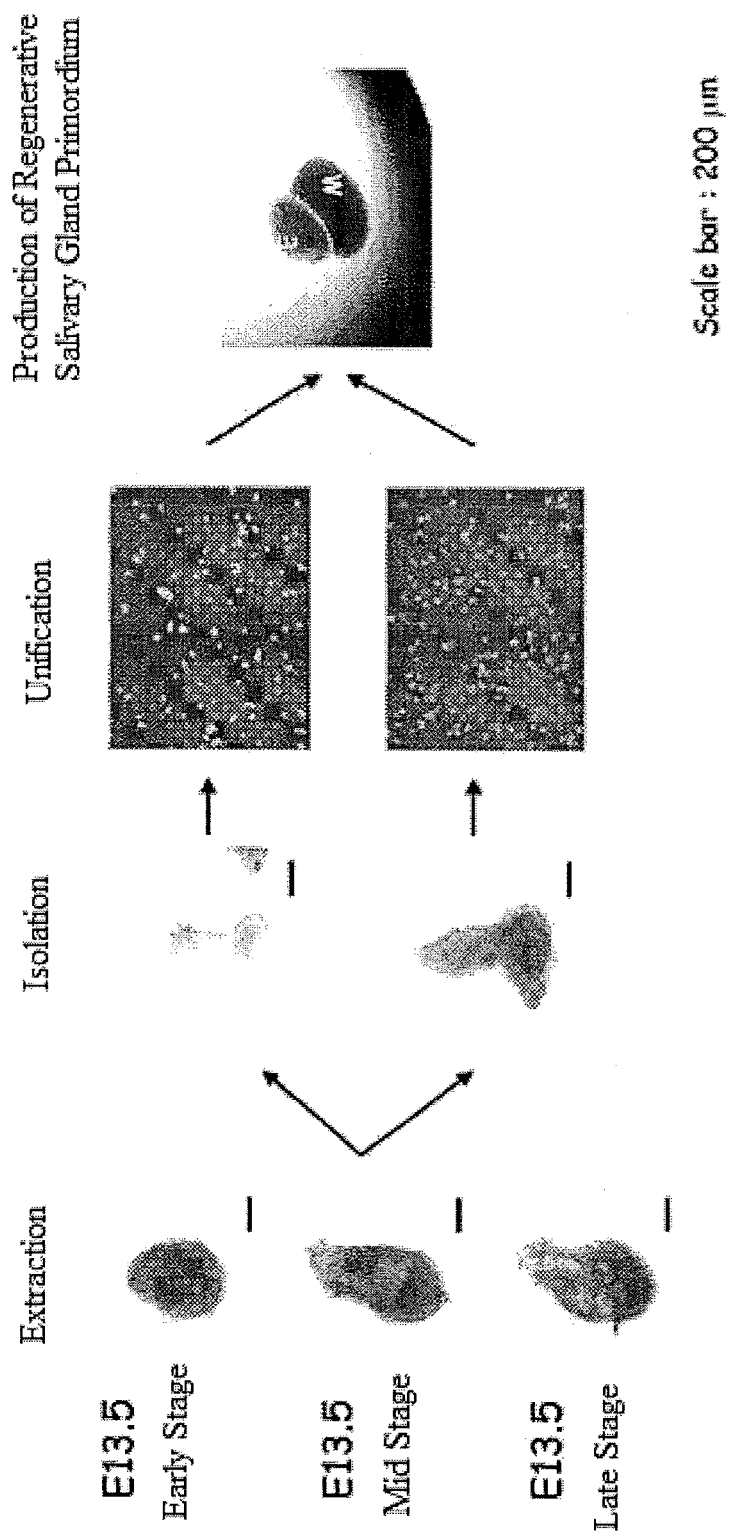

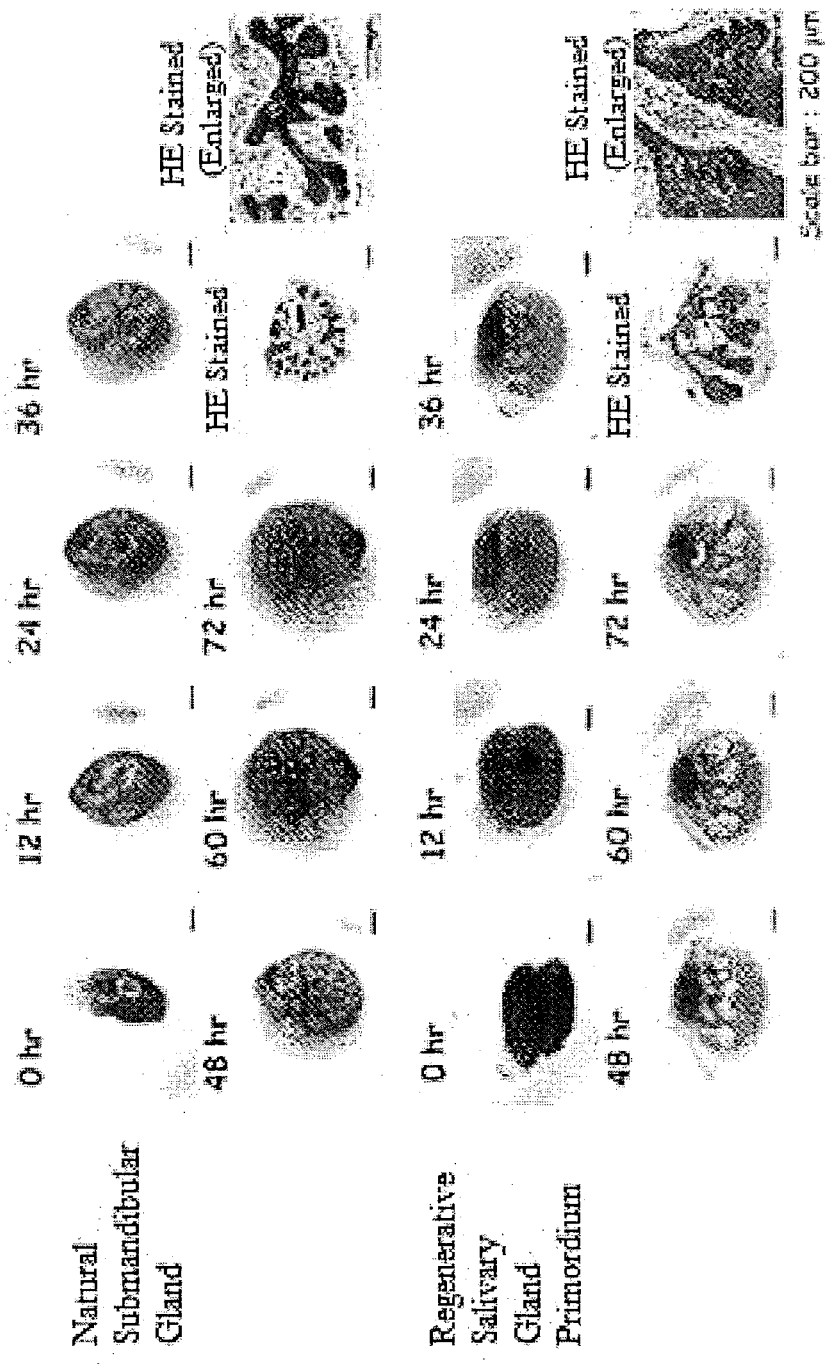
[Fig 10]

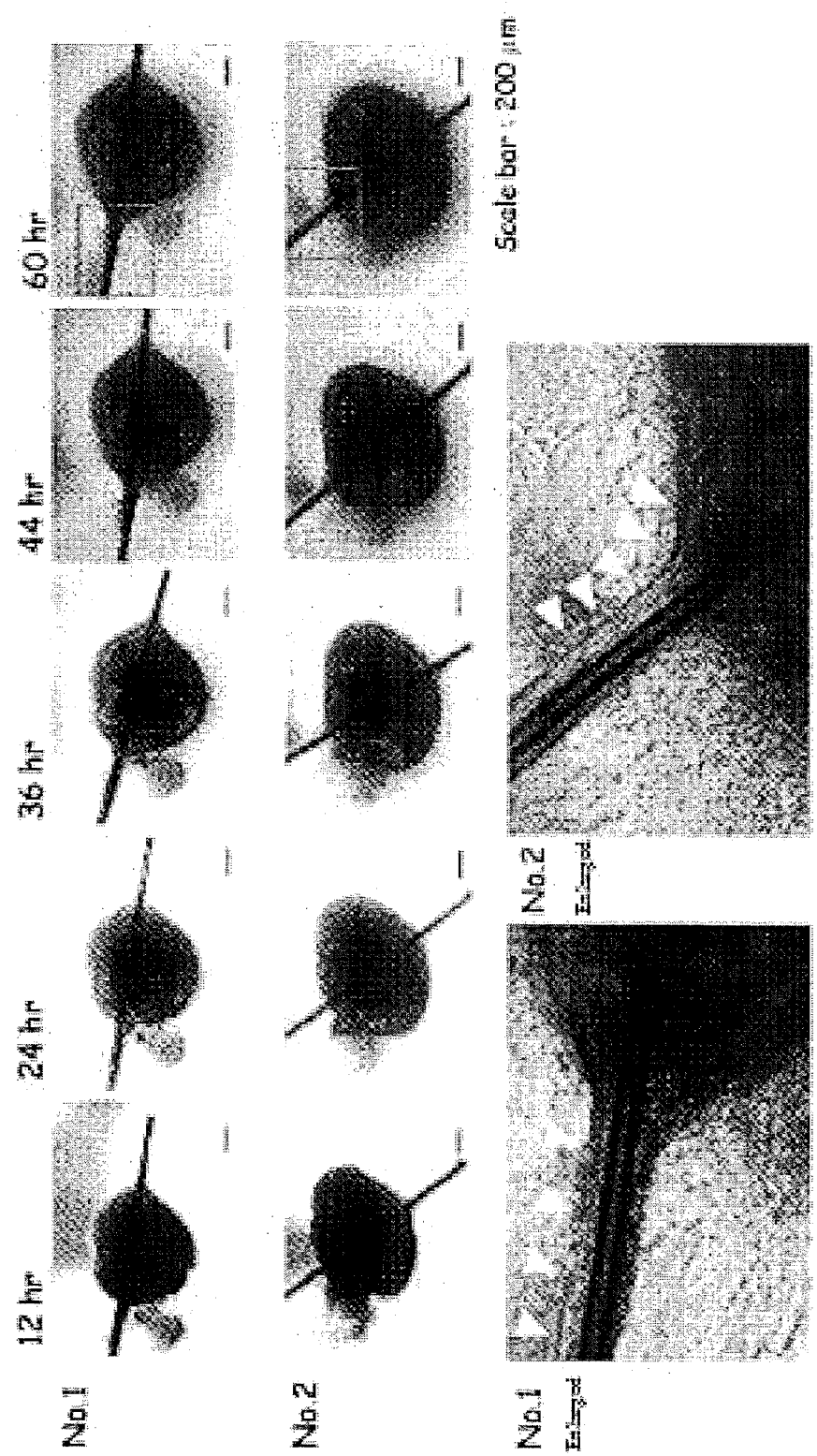
[Fig. 11]

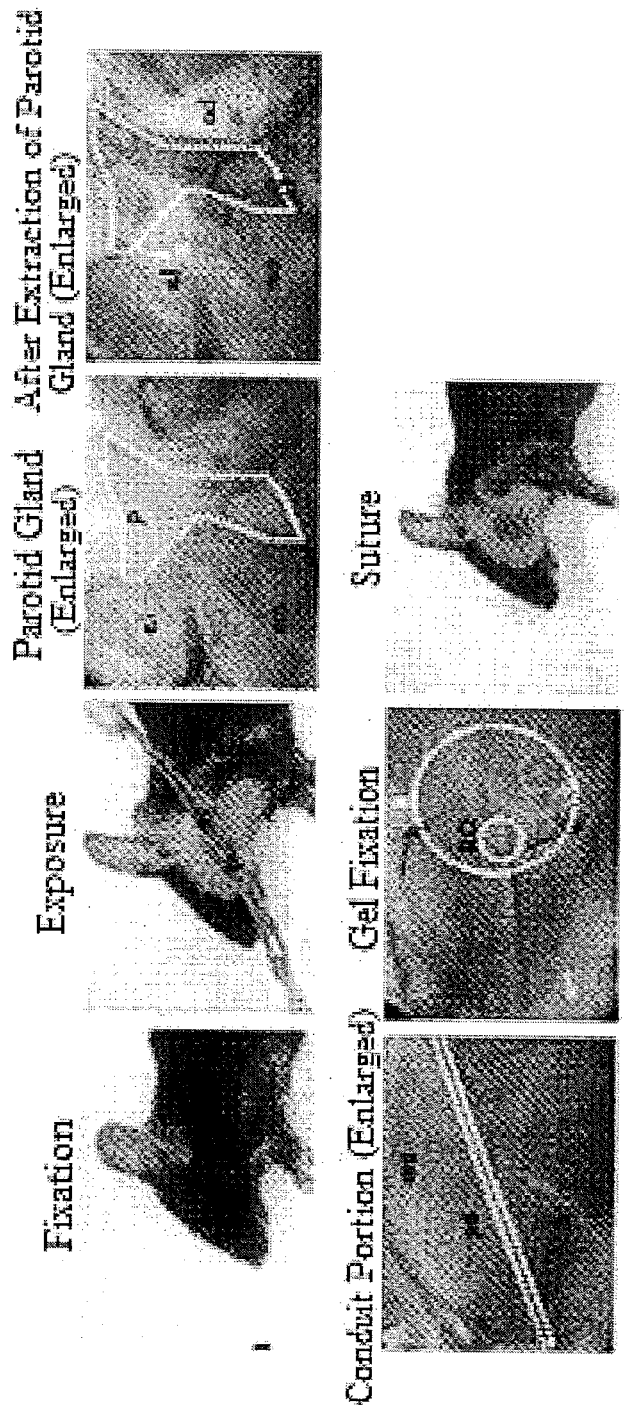
[Fig. 12]

[FIG. 13]
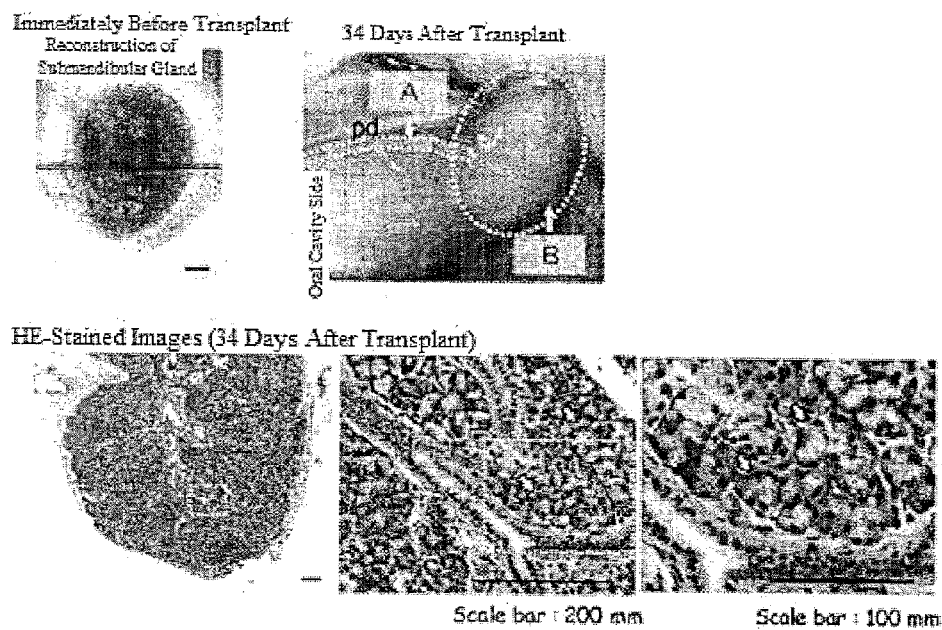
[FIG. 14]
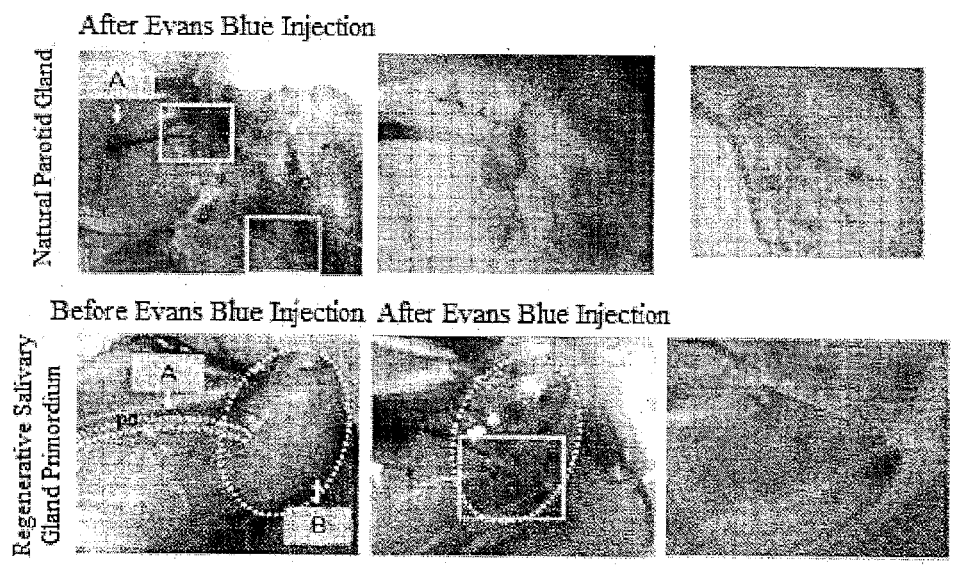

[FIG. 15]
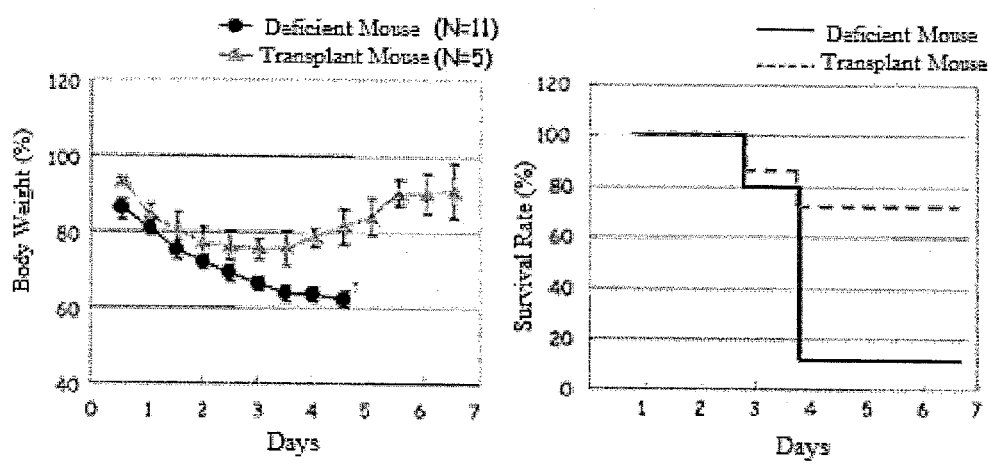
[FIG. 16]
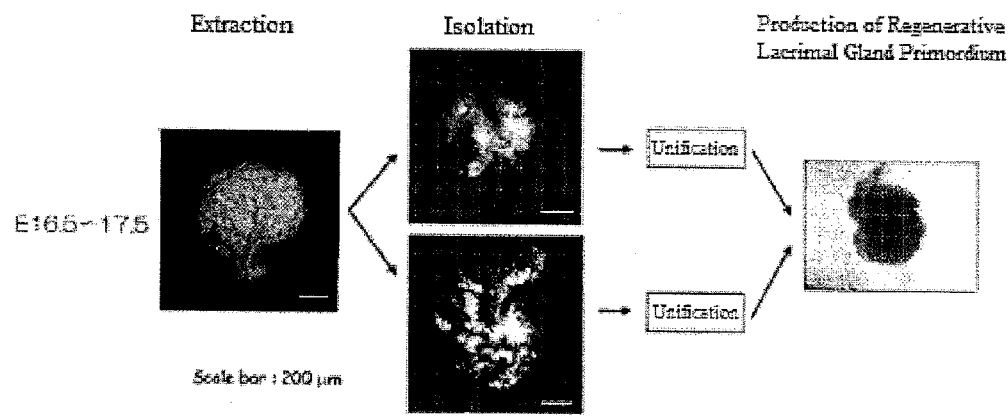

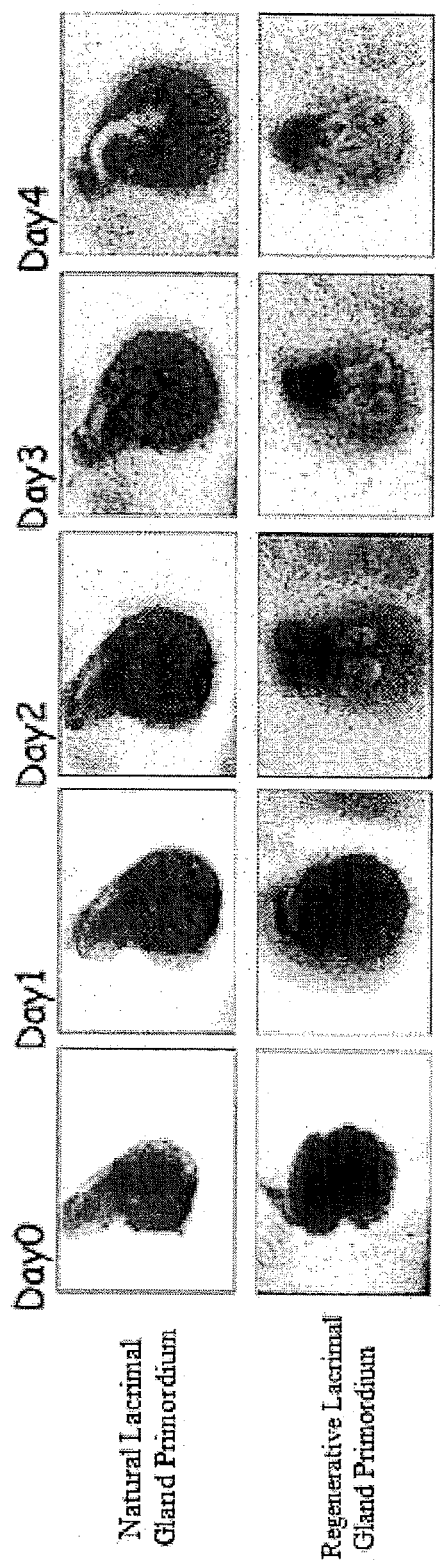
[Fig. 17]

[FIG. 18]
Immediately Before Transplant    20 Days After Transplant
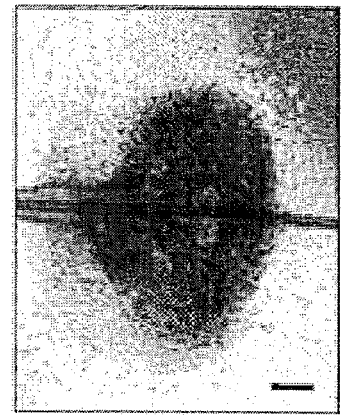 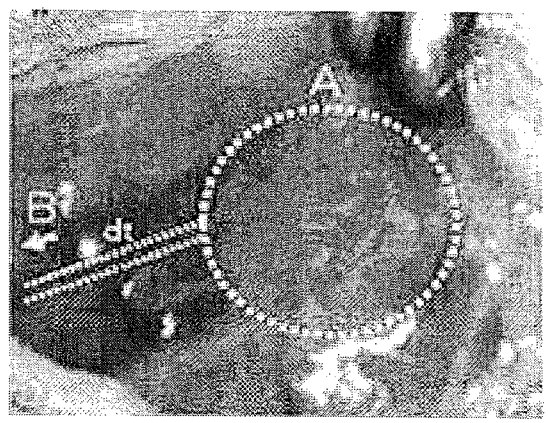

METHOD FOR PRODUCING REGENERATIVE ORGAN PRIMORDIUM PROVIDED WITH GUIDE FOR TRANSPLANTATION, COMPOSITION CONTAINING REGENERATIVE ORGAN PRIMORDIUM PROVIDED WITH GUIDE FOR TRANSPLANTATION PRODUCED THEREBY, AND METHOD FOR TRANSPLANTING REGENERATIVE ORGAN PRIMORDIUM PROVIDED WITH GUIDE FOR TRANSPLANTATION

CROSS REFERENCE TO RELATED APPLICATION

This application is a national stage application of PCT/JP2011/067045, filed on Jul. 27, 2011, which claims the priority of Japanese patent application No. 2011-026614, filed on Feb. 9, 2011. This application claims the benefit and priority of these prior applications and incorporates the contents of these prior applications by reference in their entirety.

TECHNICAL FIELD

The invention of the present application is related to a method for producing an organ germ (primordium) for transplantation in which the regenerative (bioengineered) organ germ functions in appropriate connection with the epithelial tissue on a recipient side in an organ replacement and regenerative medical technique using a regenerative organ germ, as well as a composition containing a regenerative organ germ provided with a guide for transplantation produced by the method, and a method for transplanting a regenerative organ germ provided with a guide for transplantation.

BACKGROUND ART

Regenerative medicine, in which a body part or organ which has been rendered dysfunctional due to various diseases or traumatic injuries is replaced with a regenerated body part or organ, is showing promise as a next-generation medical technique to complement medical transplantation (Non-Patent Literature 1). In past research of regenerative medicine, advances have been made in stem cell transplantation therapy in which stem cells or precursor cells are transplanted into an injured tissue or a partially dysfunctional organ to restore its function.

In regeneration of two-dimensional tissue consisting of a single type of cell, a tissue regeneration technology in which skin or corneal epithelial cells, cardiac muscle cells, and the like are organized by culturing the cells in a sheet form using cell sheet technology is nearing practical application. Therein, it is now possible to regenerate functional skin tissue by stratifying fibroblasts, which are mesenchymal cells, and skin epidermal cells to artificially reproduce a histologically-appropriate layer structure, and this technique has been clinically applied in the treatment of severe burns.

Meanwhile, it is known that in an organ, multiple types of functional cells take on a three-dimensional arrangement to express a unique function. Almost all organs are generated by interactions between epithelial cells and mesenchymal cells during the fetal period, and exhibit unique morphology and organ functions. In current regenerative medicine techniques, it is difficult to arrange multiple types of cells in a three-dimensional fashion, and a regenerative organ construct that can immediately function ex vivo has yet to be developed.

Recently, research is being conducted with the goal of organ regeneration by regenerating an organ germ and reproducing its developmental process for epithelial appendages such as teeth and salivary glands and skin appendages such as hair follicles. These organs are not directly related to the maintenance of life, but they are known to fall into organ loss or dysfunction. As an example, mention may be made of tooth loss due to dental caries, injury, and tooth germ hypoplasia, salivary secretion disorder associated with aging, and hair loss due to male pattern baldness and hair follicular dysplasia. These kinds of organ loss or dysfunction have a large impact on QOL (quality of life), and thus high expectations have been placed on functional restoration by organ regeneration. Particularly, in tooth regeneration, regeneration of a functional tooth having all of the physiological functions of a tooth has been demonstrated by transplantation of regenerative tooth germ in which epithelial cells derived from embryonic tooth germ and mesenchymal cells derived from embryonic tooth germ are appropriately arranged in a three-dimensional fashion, transplantation of a regenerative tooth unit that was ectopically regenerated in vivo, and transplantation of a functional unit containing a tooth, alveolar bone, and periodontal membrane (for example, refer to Patent Literature 1). Further, it has also been demonstrated that regenerative tooth germ or a regenerative tooth unit having similarly characteristic cell arrangement and directionality can be obtained when using oral cavity epithelial cells or primary cultured cells thereof as the epithelial cells (for example, refer to Patent Literature 2), when using amnion-derived cells as the mesenchymal cells (for example, refer to Patent Literature 3), and when using cells obtained by differentiation induction of totipotent stem cells as the mesenchymal cells (for example, refer to Patent Literature 4).

From these research results, it can be said that the feasibility of functional organ regeneration by transplantation of a regenerative organ germ or an organ regenerated from a regenerative organ germ has been demonstrated, and organ replacement and regenerative medical techniques using regenerative organ primordia are now sought for other epithelial appendages.

CITATION LIST

Patent Literature

Patent Literature 1: PCT International Publication No. WO 2006/129672
Patent Literature 2: Japanese Unexamined Patent Application, First Publication No. 2008-29756
Patent Literature 3: Japanese Unexamined Patent Application, First Publication No. 2008-206500
Patent Literature 4: Japanese Unexamined Patent Application, First Publication No. 2008-200033

Non-Patent Literature

Non-Patent Literature 1: Sharpe P T, Young C S. Test-tube teeth. Sc. Am. 293, 34-41, 2005

SUMMARY OF INVENTION

Technical Problem

It is generally known that epithelial appendages such as hair follicles and sebaceous glands, lacrimal glands, and salivary glands are generated by interaction between ectoderm-derived or endoderm-derived epithelial cells and mesoderm-derived or neural crest-derived mesenchymal cells during the fetal period.

A hair follicle, which is a skin appendage, repeats growth and regression (the hair cycle) over the individual's lifetime. The regeneration of a hair bulb during the growth period is known to be induced by a molecular mechanism similar to that in the nascent stage of the hair follicle organ. The regeneration of a hair bulb during such hair cycle is believed to be induced by hair papilla cells, which are mesenchymal cells. In the growth period, it is believed that hair follicle epithelial stem cells are differentiation-induced by hair papilla cells, which are mesenchymal cells, to regenerate a hair bulb. Since niches of neural crest-derived stem cells exist in the bulge region and the lower region, it is believed that hair follicles keep multiple stem cell niches and function as a stem cell pool. A method for culturing hair papilla cells that keep the ability to induce hair follicle formation has been reported. Although there are still no definitive reports on stem cell niches of hair follicle mesenchymal cells, the hair papilla contains cells that can differentiate into chondrocytes, blood cells, and adipocytes, and SKIPs cells that regenerate hair follicles and skin dermis can be obtained from adult skin dermal tissue, which suggests the existence of hair follicle mesenchymal stem cells. From the above, the possibility of complete organ regeneration by adult-derived cells that has not been realized in any other organs is suggested, and there are hopes for the practical application of clinically-applicable hair follicle regeneration techniques.

In order to establish hair follicle regeneration medical techniques sufficient for clinical application, the formation and elongation of hair that has a hair shaft suitable for the transplantation site and whose regenerative hair follicle has a normal tissue structure is necessary. Further, it is expected that the maintenance of stem cells by a hair follicle-specific stem cell niche and the induction of hair follicles by the hair cycle can occur, and that the hair follicles have the associated sebaceous glands and arrector muscles of hair and are functional with reactivity for piloerection by the sympathetic nerve. In the past, attempts at hair follicle regeneration have been made by regeneration of the hair follicle variable region by replacing the mesenchymal cells (hair papilla cells and dermal root sheath cells), neogenesis of the hair follicle by mesenchymal cells having hair follicle inducing ability, reconstruction of the hair follicle by epithelial/mesenchymal cells, and the like. Therein, hair follicle reconstruction and regeneration of hair follicle germ are understood as models of organ replacement and regenerative medical techniques, and it was recently demonstrated that regenerative hair follicle germ reconstructed by the organ germ method developed by the present inventors emulates normal development to regenerate hair follicles and hair. However, there has yet to be a report of a clinically-applicable hair follicle regeneration model in which hair follicles that are fully functional in vivo have been regenerated.

Hair, which is a skin appendage, is formed by skin changes, and it is produced from hair follicles formed by the interaction between two loosely-classified cell groups, that is, epithelial cells and mesenchymal cells. Therefore, the basic strategy is to regenerate hair follicles by transplanting these two types of cells onto a target skin region. In one method that has been reported for realizing this basic strategy, the entire skin including the hair follicles is regenerated by a method (graft chamber method) in which cultured hair papilla cells and newborn rat epidermal cells are mixed and transplanted onto a graft wound formed by removing the full thickness of the dorsal skin of a nude mouse. However, in this method, it is essential to form a large graft wound in order to regenerate the entire skin, making it difficult to widely implement it as a medical technique due to its highly invasive nature.

Another method has been reported in which epithelial cells and mesenchymal cells are similarly mixed and transplanted to subcutaneous tissue or under the kidney capsule to regenerate the hair follicles, and then the ectopically regenerated hair follicles are intracutaneously retransplanted. In this method, it is possible to transplant the regenerated hair follicles into the skin of a target recipient mutatis mutandis in accordance with a method based on existing hair transplantation techniques, but other body parts or organs are required as the location for regenerating the hair follicles. Also, it is known that cysts are frequently formed when epithelial cells are transplanted into subcutaneous tissue or the like, and such cysts compress the surrounding tissues which can cause pain associated with inflammation. Thus, this technique itself carries a risk of causing new diseases.

In order to solve the above-described problems, the organ germ method has been submitted in an application as a prior patent (Patent Literature 1). In this prior patent, a method is provided by which an organ can be regenerated from an artificially-produced small organ germ. In tooth regeneration, it has already been shown that normally-functioning regenerative teeth erupt in the oral cavity from a regenerative tooth germ transplanted into the jaw bone. It is believed that eruption occurs autonomously due to the growth of the regenerative tooth without any direct connection between the epithelial cells of the regenerated tooth and the oral mucosal epithelium. However, when connection with the skin epidermal layer is necessary as in the case of hair follicles, it is necessary to grow hair on the body surface from the regenerated hair follicles, and there has been a problem in that cysts can form if hair fails to grow from the transplanted hair follicles.

Skin appendages such as hair and sebaceous glands are ubiquitous in the skin and exist in extremely large numbers. In particular, hair exists in large numbers at specific sites and thus it exhibits aesthetic and functional value. Further, hair follicles, which are small organs that produce hair, are connected within the skin with appropriate directionality to the epidermal layer via pores, and function to grow hair (stems) from the body surface.

In regenerative techniques by, for example, transplantation of exocrine glands having conduits such as salivary and lacrimal glands, the transplanted salivary or lacrimal gland or the like can only exhibit its function once it is correctly linked to the recipient-side conduit through which saliva or the like passes. However, when a salivary gland or the like having a conduit is transplanted, there has been a problem in that the transplanted gland fails to function because it cannot correctly link to the recipient-side conduit.

In other words, it is understood that when regenerating epithelial appendages such as hair follicles or a salivary gland, connection with appropriate directionality and manner between the recipient-side epithelial tissue and the regenerated organ is extremely important for the exertion of the regenerated organ's function.

Solution to Problem

As described above, in order to regenerate epithelial appendages such as hair follicles, sebaceous glands, salivary glands, and lacrimal glands and enable them to exert a prescribed function, several transplants must be connected appropriately with the recipient. As a result of keen examination in order to solve the above-described problems, the present inventors discovered the inter-epithelial tissue-connecting plastic method, in which an organ germ regenerated by the organ germ method is connected to a recipient tissue via a guide. The present inventors further discovered that this method enables the direction of the polarity of the regenerative organ germ to be ensured and the adhesion with the recipient side after transplantation to be improved, and enables the regenerated organ to appropriately link with the recipient to be functionally regenerated.

Namely, the present invention is related to a method for producing a regenerative organ germ provided with a guide for transplantation, comprising: preparing a regenerative organ germ by closely contacting a first cell mass which substantially consists of mesenchymal cells and a second cell mass which substantially consists of epithelial cells and culturing these cell masses within a support, and inserting the guide into the regenerative organ germ.

Herein, in one embodiment of the method for producing a regenerative organ germ provided with a guide for transplantation of the present invention, the method comprises further culturing the regenerative organ germ for several days after inserting the guide.

In one embodiment of the method for producing a regenerative organ germ provided with a guide for transplantation of the present invention, at least one of the first and second cell masses is derived from an organ which is the target of regeneration.

In one embodiment of the method for producing a regenerative organ germ provided with a guide for transplantation of the present invention, the first cell mass and the second cell mass are both derived from an organ which is the target of regeneration.

In one embodiment of the method for producing a regenerative organ germ provided with a guide for transplantation of the present invention, the regenerative organ germ is an epithelial appendage germ.

In one embodiment of the method for producing a regenerative organ germ provided with a guide for transplantation of the present invention, the regenerative organ germ is any one of organ primordia selected from the group consisting of regenerative hair follicle germ, regenerative sweat gland germ, regenerative sebaceous gland germ, regenerative salivary gland germ, regenerative mammary gland germ, regenerative renal nephron germ, regenerative lacrimal gland germ, and regenerative endocrine gland germ.

In one embodiment of the method for producing a regenerative organ germ provided with a guide for transplantation of the present invention, the regenerative organ germ is a regenerative hair follicle germ, and the epithelial cells are bulge region epithelial cells or hair matrix basal epithelial cells.

In one embodiment of the method for producing a regenerative organ germ provided with a guide for transplantation of the present invention, the regenerative organ germ is a regenerative hair follicle germ, and the mesenchymal cells are hair papilla cells or dermal root sheath cells.

In one embodiment of the method for producing a regenerative organ germ provided with a guide for transplantation of the present invention, the regenerative organ germ is a regenerative salivary gland germ, and the epithelial cells are salivary gland-derived epithelial cells and the mesenchymal cells are salivary gland-derived mesenchymal cells.

In one embodiment of the method for producing a regenerative organ germ provided with a guide for transplantation of the present invention, the regenerative organ germ is a regenerative lacrimal gland germ, and the epithelial cells are lacrimal gland-derived epithelial cells and the mesenchymal cells are lacrimal gland-derived mesenchymal cells.

In one embodiment of the method for producing a regenerative organ germ provided with a guide for transplantation of the present invention, the guide is a chemical fiber.

In one embodiment of the method for producing a regenerative organ germ provided with a guide for transplantation of the present invention, the guide is bioabsorbable.

In one embodiment of the method for producing a regenerative organ germ provided with a guide for transplantation of the present invention, the guide is a nylon thread.

Also, according to another embodiment of the present invention, the present invention is related to a composition comprising a regenerative organ germ provided with a guide for transplantation produced by a method for producing a regenerative organ germ provided with a guide for transplantation.

Also, according to another embodiment of the present invention, the present invention is related to a method for transplantation of a regenerative organ germ for transplantation comprising transplanting a regenerative organ germ provided with a guide for transplantation produced by a method for producing a regenerative organ germ provided with a guide for transplantation into a target site.

Herein, in one embodiment of the method for transplantation of a regenerative organ germ provided with a guide for transplantation of the present invention, a portion on the epithelial cell side of the transplanted regenerative organ germ and the epithelial cells of the target elongate and connect along the guide by maintaining the guide in a state in which it protrudes from a transplant site.

Also, in one embodiment of the method for transplantation of a regenerative organ germ provided with a guide for transplantation of the present invention, the regenerative organ germ is an organ germ intended for regeneration of an organ having a conduit, and during transplantation of the regenerative organ germ, the guide is inserted into a conduit existing in the target site and a portion on the epithelial cell side of the regenerative organ germ and the conduit are connected, and thereby the portion on the epithelial cell side of the regenerative organ germ elongates along the guide and connects to the conduit of the target site.

Effects of the Invention

The present invention can provide a regenerative organ germ for transplantation that can improve adhesion while ensuring the direction of the polarity of the regenerative organ germ and retaining appropriate directionality relative to the recipient-side epithelial tissue after transplantation. Also, the regenerative organ germ for transplantation produced by the present invention has a guide, and thus the operation during transplantation can be simplified and the depth and transplant direction and the like can be easily adjusted during transplantation.

Also, since the epithelial cells of the regenerative organ germ and the recipient-side epithelial layer (epithelial cells) are connected along the guide, the formation of cysts derived from the regenerative organ germ can be suppressed, especially in the course of hair follicle formation. Also, in an exocrine gland or the like having a conduit such as a salivary gland, the epithelial cells elongate along the guide, and thus the connection efficiency with the recipient-side conduit can be improved.

Further, the regenerative organ germ produced by the present invention can be applied to epithelial appendages including hair follicles, sweat glands, salivary glands, and the like, and it is not limited to the regeneration of a body surface and can be applied in the regeneration of organs that are connected to a lumen such as in the oral cavity, the intestinal tract, or an endocrine tissue, via a luminal structure. Since the present invention can be applied to the regeneration of these organs and tissues as well, it provides a technique that is applicable not only to skin appendages but also to regenerative medicine for a wide variety of organs and tissues.

BRIEF DESCRIPTION OF DRAWINGS

FIG. 1 is a schematic view illustrating a production flow of a regenerative hair follicle germ for transplantation using mouse embryonic epithelium-derived epithelial cells and mouse embryonic epithelium-derived mesenchymal cells, which is one embodiment of the present invention.

FIG. 2 shows the state immediately after, three days after, and ten days after transplantation of the regenerative hair follicle germ for transplantation produced by the mouse embryonic epithelium-derived epithelial cells and mesenchymal cells into a recipient epithelium. The upper row shows photos of the epithelium, and the lower row shows the results upon HE-staining a section of the transplant site and observing it under a fluorescent microscope.

FIG. 3 is a schematic view illustrating a production flow of a regenerative hair follicle germ for transplantation using mouse adult whisker-derived bulge region epithelial cells and mouse adult whisker-derived cultured papilla cells, which is one embodiment of the present invention.

FIG. 4A shows the state of insertion of a guide into a regenerative hair follicle germ during culture. FIG. 4B shows the transplant site (indicated by the arrow) immediately after transplantation of the regenerative hair follicle germ. FIG. 4C shows the transplant site 21 days after transplantation.

FIG. 5 shows the results upon HE-staining a tissue section of a hair follicle regenerated by transplantation of a mouse adult whisker-derived regenerative hair follicle germ (top row), and the results upon observing the GFP fluorescence in a tissue section of the regenerated hair follicle (lower row).

FIG. 6a shows a photo of a cross-section of a regenerated regenerative whisker captured with an optical microscope after transplantation of a mouse adult whisker-derived regenerative hair follicle for transplantation, which is one embodiment of the present invention. FIG. 6b shows a photo of the surface of a hair shaft of the regenerative whisker captured with an electron microscope.

FIG. 7 shows the state 27 days after, 31 days after, 41 days after, and 46 days after transplantation of a mouse regenerative whisker grown by transplantation of a regenerative hair follicle for transplantation, which is one embodiment of the present invention. The growth of individual regenerative hairs (the distinguished regenerative hairs are shown by the arrow mark and the triangle mark) is tracked, respectively.

FIG. 8 is a graph illustrating the hair cycle of a regenerative whisker. The growth period and the regression period from the first hair growth through the third hair growth are illustrated, respectively. The "Control" indicates the average of three hair cycles tracked after transplanting a natural mouse whisker onto the back of a nude mouse and regrowing it.

FIG. 9 is a schematic view illustrating a production flow of a regenerative salivary gland germ for transplantation using mouse embryonic submandibular gland epithelial tissue-derived epithelial cells and mouse embryonic submandibular gland mesenchymal tissue-derived mesenchymal cells, which is one embodiment of the present invention. In FIG. 9, the epithelial tissue isolated from an extracted submandibular gland germ is shown in the upper row of photos, and the mesenchymal tissue isolated from a submandibular gland germ is shown in the lower row of photos. In the photos showing the regenerative salivary gland germ produced in FIG. 9, "E" indicates a cell mass of epithelial cells and "M" indicates a cell mass of mesenchymal cells. As shown in FIG. 9, submandibular gland primordia at different stages of development (early, mid, late) were obtained from a mouse embryo at a gestational age of 13.5 days.

FIG. 10 shows photos captured with an optical microscope depicting the state of a salivary gland germ and a regenerative salivary gland germ at several times (start of culture, after 12 hours of culture, after 24 hours of culture, after 36 hours of culture, after 48 hours of culture, after 60 hours of culture, after 72 hours of culture) during the organ culture of a submandibular gland extracted from a mouse embryo and a regenerative salivary gland germ for transplantation produced using mouse embryonic submandibular gland epithelial tissue-derived epithelial cells and mouse embryonic submandibular gland mesenchymal tissue-derived mesenchymal cells. The results upon HE-staining the regenerative salivary gland germ 72 hours after culture are also shown.

FIG. 11 shows photos captured with an optical microscope depicting the state of a regenerative salivary gland germ at several elapsed times (after 12 hours of culture, after 24 hours of culture, after 36 hours of culture, after 44 hours of culture, after 60 hours of culture) during a 60-hour organ culture upon inserting a bioabsorbable thread as a guide into a regenerative salivary gland germ for transplantation produced using mouse embryonic submandibular gland epithelial tissue-derived epithelial cells and mouse embryonic submandibular gland mesenchymal tissue-derived mesenchymal cells. The bottommost row of photos shows the regenerative salivary gland germ after 60 hours of the organ culture. Therein, the epithelial cell side of the regenerative salivary gland germ has begun to move/elongate along the guide thread to exhibit a conduit-like structure (portion marked by arrows).

FIG. 12 shows photos depicting each step (fixation, exposure of parotid gland conduit portion, extraction of parotid gland, fixation of gel, and suture) when transplanting a regenerative salivary gland germ with a guide for transplantation produced using mouse embryonic submandibular gland epithelial tissue-derived epithelial cells and mouse embryonic submandibular gland mesenchymal tissue-derived mesenchymal cells into a conduit portion of a parotid gland of an adult mouse. In FIG. 12, "el" indicates a lacrimal gland, "ma" indicates a masseter, "p" indicates a parotid gland, "od" indicates an adipose tissue, "pd" indicates a parotid gland conduit, and "RO" indicates a regenerative submandibular gland.

FIG. 13 The upper row in FIG. 13 shows photos captured with an optical microscope depicting the state immediately before transplantation of a regenerative salivary gland germ with a guide for transplantation produced using mouse embryonic submandibular gland epithelial tissue-derived epithelial cells and mouse embryonic submandibular gland mesenchymal tissue-derived mesenchymal cells and the state 34 days after transplantation into a conduit portion of a parotid gland of an adult mouse from which the parotid gland was removed. In these photos, "A" indicates a conduit that extends from the transplanted regenerative salivary gland germ, "B" indicates the transplanted regenerative salivary gland germ, and "pd" indicates the parotid gland. The lower row in FIG. 13 shows the results upon HE-staining the regenerative submandibular gland 34 days after transplantation. The arrows therein indicate serous acinar cell-like cells.

FIG. 14 shows photos captured upon injecting Evans blue from the conduit side into a regenerative salivary gland germ 30 days after transplantation into an adult mouse. In FIG. 14, "A" indicates the site of Evans blue injection and "B" indicates the transplant site of the regenerative submandibular gland.

FIG. 15 is a graph illustrating a comparison of transitions in weight and survival rate between a salivary gland-deficient mouse from which all of the salivary glands were removed and a mouse from which all of the salivary glands were removed and then a regenerative salivary gland germ with a guide of the present invention was transplanted to a submandibular gland site.

FIG. 16 is a schematic view illustrating a production flow of a regenerative lacrimal gland germ for transplantation using mouse embryonic lacrimal gland epithelial tissue-derived epithelial cells and mouse embryonic lacrimal gland mesenchymal tissue-derived mesenchymal cells, which is one embodiment of the present invention. The photo on the left was captured under a stereomicroscope and depicts a lacrimal gland germ extracted from a mouse embryo at a gestational age of 16.5 to 17.5 days. The other photos were captured under a stereomicroscope and depict an epithelial tissue isolated from the lacrimal gland germ (the upper photo in the middle column), a mesenchymal tissue isolated from the lacrimal gland germ (the lower photo in the middle column), and a regenerative lacrimal gland germ that was reconstructed (photo on the right).

FIG. 17 shows photos captured with an optical microscope depicting the state of a lacrimal gland germ and a regenerative lacrimal gland germ at several times (start of culture, after 1 day of culture, after 2 days of culture, after 3 days of culture, after 4 days of culture) during the organ culture of a lacrimal gland germ extracted from a mouse embryo and a regenerative lacrimal gland germ for transplantation produced using mouse embryonic lacrimal gland epithelial tissue-derived epithelial cells and mouse embryonic lacrimal gland mesenchymal tissue-derived mesenchymal cells.

FIG. 18 shows photos captured with an optical microscope depicting the state immediately before transplantation of a regenerative lacrimal gland germ with a guide for transplantation produced using mouse embryonic lacrimal gland epithelial tissue-derived epithelial cells and mouse embryonic lacrimal gland mesenchymal tissue-derived mesenchymal cells and the state 20 days after transplantation into a conduit portion of a lacrimal gland of an adult mouse from which the acinar portion of the lacrimal gland was removed. In these photos, "A" indicates a portion at which the transplanted regenerative lacrimal gland germ adhered, "B" indicates the direction of the eye, and "dt" indicates a conduit of the lacrimal gland.

DESCRIPTION OF EMBODIMENTS

The embodiments of the present application will be explained below in detail.

A first embodiment of the production method according to the present invention is a method for producing a regenerative organ germ for transplantation into a mammal (for example, a human being), including inserting a guide into the regenerative organ germ during culture produced by organ culture of mesenchymal cells and epithelial cells.

In the present specification, "mesenchymal cells" indicate cells derived from mesenchymal tissue and cells obtained by culturing such mesenchymal tissue-derived cells, and "epithelial cells" indicate cells derived from an epithelial tissue and cells obtained by culturing such epithelial tissue-derived cells.

Also, in the present specification, "epithelial appendages" refer to organs formed by interaction between ectoderm-derived or endoderm-derived epithelial cells and mesoderm-derived or neural crest-derived mesenchymal cells, such as endodermal epithelium-derived organs, ectodermal appendages, endocrine glands, and exocrine glands connected to other epithelial tissue via a conduit or the like. More specifically, "epithelial appendages" indicate, for example, epidermal appendages such as hair follicles, sweat glands, lacrimal glands, and sebaceous glands, as well as organs that are connected to a lumen such as in the oral cavity, the intestinal tract, or an endocrine tissue, via a luminal structure.

Also, in the present specification, "ectodermal appendages" indicate ectoderm-derived organs among the "epithelial appendages", such as epidermal appendages like hair follicles, sweat glands, lacrimal glands, sebaceous glands, and the like.

Next, the regenerative organ germ used in the method of the present invention will be explained.

The regenerative organ germ can be produced by a method including: closely contacting a first cell mass which substantially consists of mesenchymal cells and a second cell mass which substantially consists of epithelial cells and culturing these cell masses within a support.

The "closely contacting a first cell mass which substantially consists of mesenchymal cells and a second cell mass which substantially consists of epithelial cells and culturing these cell masses within a support" is described in, for example, Patent Literatures 1 to 4 as well as Japanese Unexamined Patent Application, First Publication No. 2008-29757, and the disclosures of each of these publications are incorporated in their entirety for reference into the present specification. In the present specification, when producing, for example, a hair follicle germ by the above-described method, the produced hair follicle germ will be referred to as a "regenerative hair follicle germ".

The first cell mass and the second cell mass each substantially consist of only mesenchymal cells or only epithelial cells. In the present invention, the phrase "substantially consists of only mesenchymal cells" means that the cell mass performs a function identical to a cell mass that consists of only mesenchymal cells. It preferably indicates a state in which the cell mass does not include anything other than cells which are mesenchymal cells as far as possible. Also, the cell mass can include cells of different types as long as they are mesenchymal cells. The same applies to the phrase "substantially consists of only epithelial cells".

Herein, a cell mass refers to a state in which cells are closely adhered, and it may be a tissue or a cell aggregate prepared from discrete cells. The use of a tissue is advantageous because it is easy to obtain an organ with correct cell arrangement and shape, but there may be constraints on the amount that can be obtained. Cultured cells can also be used to prepare a cell aggregate, and a cell mass is relatively easy to obtain when using cultured cells, making cultured cells preferable at least from this perspective.

At least one of the mesenchymal cells and the epithelial cells used in the present invention is preferably derived from the organ (including a tissue belonging to the organ) which is the target of regeneration. Thereby, the target organ can be easily formed using cells which are already oriented to the target organ. Also, in order to produce the target organ more reliably, it is most preferable for both the mesenchymal cells and the epithelial cells to be derived from the organ which is the target of regeneration.

One example of a regenerative organ germ which is the subject of the present invention can be an organ germ of an epithelial appendage. However, the present invention is not limited thereto, and other examples can include regenerative hair follicle germ, regenerative sweat gland germ, regenerative sebaceous gland germ, regenerative salivary gland germ, regenerative mammary gland germ, regenerative renal nephron germ, regenerative lacrimal gland germ, and regenerative endocrine gland germ. When producing these regenerative organ primordia, mesenchymal cells or epithelial cells derived from the target organ can be used, and mesenchymal cells or epithelial cells obtained by the induction of undifferentiated cells can also be used. For example, when producing a regenerative hair follicle germ, hair papilla cells, dermal root sheath cells, nascent skin mesenchymal cells, and hair follicle mesenchymal cells induced from iPS cells or ES cells can be used as the mesenchymal cells, and outer root sheath outermost layer cells of the bulge region, hair matrix basal epithelial cells, and hair follicle epithelial cells induced from iPS cells or ES cells can be used as the epithelial cells. Also, when producing a regenerative sweat gland germ, mesenchymal cells of nascent skin, hair follicle dermal clump cells, and skin mesenchymal cells induced from iPS cells or ES cells can be used as the mesenchymal cells, and epithelial cells of nascent skin and sweat gland epithelial cells induced from iPS cells or ES cells can be used as the epithelial cells. Also, when producing a regenerative salivary gland germ, mesenchymal cells of a nascent salivary gland germ or salivary gland mesenchymal cells induced from iPS cells or ES cells can be used as the mesenchymal cells, and epithelial cells of a salivary gland intercalated portion and salivary gland epithelial cells induced from iPS cells or ES cells can be used as the epithelial cells. Also, when producing a regenerative lacrimal gland germ, mesenchymal cells of a nascent lacrimal gland germ or lacrimal gland mesenchymal cells induced from iPS cells or ES cells can be used as the mesenchymal cells, and epithelial cells of a nascent lacrimal gland germ and lacrimal gland epithelial cells induced from iPS cells or ES cells can be used as the epithelial cells.

Also, the organ from which the mesenchymal cells and epithelial cells are taken preferably retain the ability to regenerate in a normal adult body from the perspective of juvenility and homogeneity in the cell differentiation stage. Also, an organ which has been equipped with the ability to regenerate by artificial surgical operation, drug administration, or gene introduction can also be used.

Cells derived from other mesenchymal tissue in vivo can also be used as mesenchymal cells derived from somewhere other than the organ which is the target of regeneration. Preferably, such cells are bone marrow cells that do not include blood cells or mesenchymal cells, and further preferably mesenchymal cells from within the oral cavity, bone marrow cells from within the jaw bone, mesenchymal cells derived from cranial neural crest cells, mesenchymal precursor cells or stem cells thereof that can differentiate into such mesenchymal cells, and the like. Patent Literature 3 describes an example in which amnion-derived cells are used as the mesenchymal cells, and Patent Literature 4 describes an example in which cells obtained by differentiation induction of totipotent stem cells are used, as the mesenchymal cells. The disclosures in these publications are incorporated in their entirety for reference into the present specification.

Cells derived from other epithelial tissue in vivo can also be used as epithelial cells derived from somewhere other than the organ which is the target of regeneration. Preferably, such cells are epithelial cells of skin or of mucous membranes and gums in the oral cavity, and are further preferably immature epithelial precursor cells, for example, non-keratinized epithelial cells or stem cells thereof that can differentiate into epithelial cells which have differentiated, e.g. keratinized, or parakeratinized, like the skin or mucous membranes or the like. Patent Literature 2 describes an example in which oral cavity epithelial cells or primary cultured cells thereof are used as the epithelial cells, and the disclosures therein are incorporated in their entirety for reference into the present specification. From the perspective of the use of autogenous tissue, it is preferable to use mesenchymal cells and epithelial cells or tissue including these cells from the target of transplantation.

The mesenchymal cells and epithelial cells or tissue including these cells for producing the regenerative organ germ can be collected from mammals such as primates (e.g. humans, monkeys, etc.) and ungulates (e.g. pigs, cows, horses, etc.), small mammals such as rodents (e.g. mice, rats, rabbits, etc.), as well as various other animals such as dogs and cats. The collection of mesenchymal cells and epithelial cells or tissue including these cells may be carried out by extracting under aseptic conditions and storing in an appropriate storage solution, while applying the conditions normally used for tissue collection without change.

The mesenchymal cells and epithelial cells from the organ (including a tissue belonging to the organ) which is the target of regeneration are prepared by, for example, first separating the organ (including a tissue belonging to the organ) which has been isolated from surrounding tissue into a mesenchymal tissue and an epithelial tissue in accordance with its shape. When doing so, an enzyme can be used to facilitate the separation. As the enzyme, mention may be made of known enzymes such as dispase, collagenase, and trypsin, and those skilled in the art can use an appropriate enzyme of their choice.

A cell aggregate in the present invention means an aggregation of cells derived from a mesenchymal tissue or an epithelial tissue, and it can be prepared by aggregating cells obtained by dispersing a mesenchymal tissue or an epithelial tissue into discrete cells or aggregating cells obtained by primary culture or subculture of such cells.

In order to disperse cells, an enzyme such as dispase, collagenase, and trypsin can be used. When performing a primary culture or subculture of dispersed cells before preparing a cell aggregate in order to obtain a sufficient number of cells, a medium that is generally used in culturing animal cells such as Dulbecco's Modified Eagle Medium (DMEM) can be used as the medium for culture. Serum can be added in order to promote cell growth, or as an alternative for serum, for example, a cell growth factor such as FGF, EGF, and PDGF or a known serum component such as transferrin can be added. When adding serum, the concentration can be appropriately modified depending on the state of the culture at the time of addition, but it can normally be set to around 10%. For the cell culture, normal culture conditions are applied, for example culture in an incubator having 5% $CO_2$ concentration at a temperature of about 37° C. Further, an antibiotic such as streptomycin can also be added as appropriate.

In order to aggregate cells, for example, a cell suspension can be centrifuged. In a cell aggregate of mesenchymal cells and epithelial cells, the respective cells are preferably in a high density state in order to ensure that the cells reliably interact with each other when they are brought into close contact. A high density state means a degree of density equivalent to that when constituting a tissue, for example $5\times10^7$ cells/ml to $1\times10^9$ cells/ml, preferably $1\times10^8$ cells/ml to $1\times10^9$ cells/ml, and most preferably $2\times10^8$ cells/ml to $8\times10^8$ cells/ml. The method for achieving high density of the cell aggregate is not particularly limited, but, for example, it can be achieved by a method in which the cells are aggregated by centrifugation and then precipitated. Centrifugation is preferred because it can easily achieve high density without compromising the activity of the cells. Centrifugation can be carried out for 3 to 10 minutes at the number of rotations that provides a centrifugal force of 300×g to 1200×g and preferably 500×g to 1000×g. If the centrifugation is less than 300×g, the cell density tends not to reach a sufficiently high level, whereas if the centrifugation is greater than 1200×g, the cells may be damaged.

When preparing a high-density cell aggregate by centrifugation, a cell suspension is normally prepared in a container such as a tube used for centrifugation of cells and then the cells are centrifuged. After centrifugation, the cells remain as a precipitate and as much of the supernatant is removed as possible. At this time, the amount of components other than the target cells (e.g., culture solution, buffer, etc.) is preferably equal to or less than the capacity of the cells, and most preferably no components other than the target cells are included. If these kind of high-density cell masses are brought into close contact within a support carrier by a method to be explained below, the cells make tight contact with each other and cell-cell interaction is effectively exhibited.

The support carrier is not particularly limited as long as the cell culture can be carried out therein. For example, gelled, fibrous, and solid-state support carriers are preferred. By using such a support carrier, excessive pressure on the regenerative organ germ in vivo can be further prevented.

As the support carrier to be used in the present invention, mention may be made of, for example, collagen, agarose gel, carboxymethyl cellulose, gelatin, agar, hydrogel, Cell Matrix (product name), Mebiol Gel (product name), Matrigel (product name), elastin, fibrin, laminin, extracellular matrix mixture, polyglycolic acid (PGA), polylactic acid (PLA), lactic acid/glycolic acid copolymer (PLGA), and the like. Among others, collagen, agarose gel, carboxymethyl cellulose, gelatin, agar, hydrogel, Cell Matrix, Mebiol Gel, Matrigel, extracellular matrix mixture, elastin, fibrin, and laminin, which have appropriate hardness and retentivity, are preferred.

For example, a liquid support carrier can be used by curing after disposing the regenerative organ germ therein. For example, by preparing a collagen gel drop on a culture dish, disposing the regenerative organ germ in the collagen drop, and then culturing within a $CO_2$ incubator at 37° C., the collagen can be gelled.

The support carrier used for the purpose of culturing the first and second cell masses preferably has a retentivity sufficient to retain the close contact state of the cell masses without dispersion of the cells. Herein, the "close contact state" means a state in which the high-density cell masses of mesenchymal cells and epithelial cells described above maintain an equally high density even near the contact surface between the mesenchymal cells and the epithelial cells. If the support carrier capable of retaining a close contact state is, for example, collagen, appropriate hardness can be provided by using the collagen at a concentration such that the final concentration is 2 mg/ml to 3 mg/ml, or in other words a concentration such that the jelly strength is 120 g to 250 g according to a method mutatis mutandis in accordance with JIS-K6503-1996 (measured as a load necessary to depress a 12.7 mm diameter plunger by 4 mm). Other types of support carriers can be preferably used as the support carrier of the present invention as long as they have equivalent strength according to an equivalent evaluation method. Also, a support carrier having a hardness corresponding to the intended jelly strength can be obtained by mixing one or more types of support carriers.

The method for disposing the first and second cell masses in the support carrier is not particularly limited. If the cell masses are cell aggregates, for example, a precipitate obtained by centrifugation as described above can be disposed by inserting it into the support carrier with a microsyringe or the like. If the cell masses are a tissue, they can be disposed at an arbitrary location in the support carrier using the tip of a syringe needle or the like.

The method for disposing the first and second cell masses in close contact in the support carrier in the present invention is not particularly limited. For example, the cell masses can be brought into close contact by disposing one of the cell masses in the support carrier and then disposing the other cell mass so that it presses against the one cell mass. More specifically, one of the cell masses can be pressed against the other cell mass by appropriately changing the position of the tip of the above syringe needle in the support carrier. When using an epithelial tissue or a mesenchymal tissue as the cell masses, it is preferable to dispose the surface of the epithelial tissue or mesenchymal tissue at which the tissue had been in contact with the mesenchymal tissue or epithelial tissue, respectively, in the original organ (including a tissue belonging to the organ) so that it contacts the other cell mass.

It is also preferable to include solidifying the support carrier after disposing the cell masses. Thereby, the cells aggregate further and a state of even higher density can be achieved. For example, when using collagen gel, it can be solidified by allowing it to stand for several minutes to several tens of minutes at the culture temperature. At this time, the fewer components other than cells there are in the cell masses, the higher the density which can be realized.

The culture duration differs depending on the number of cells disposed within the support carrier, the state of the cell masses, the culture conditions, the type of animal, and the like, and the duration can be appropriately chosen by a person skilled in the art. The culture duration can also be appropriately modified depending on the organ that is the target of regeneration.

By increasing the culture duration, the formation of the regenerative organ germ can be further progressed. In order to obtain a desired condition, for example, the culture can be carried out for 6 days or more, 30 days or more, 50 days or more, 100 days or more, or 300 days or more, and the medium and culture conditions can be changed during the culture.

For example, when transplanting a regenerative hair follicle germ, in order to obtain functional hair, the regenerative hair follicle germ is preferably cultured for at least one day, and more preferably cultured 2 or more days.

When transplanting a regenerative salivary gland germ or a regenerative lacrimal gland germ to obtain a functional salivary gland or lacrimal gland, the regenerative salivary gland germ or regenerative lacrimal gland germ is preferably cultured for at least one day, and more preferably cultured 2 or more days.

For the culture process within the support carrier, a support carrier including the first and second cell masses can be cultured alone or cultured in the presence of other animal cells or the like.

When culturing the support carrier alone, conditions which are generally used for culture of animal cells can be used as the culture conditions. Mammal-derived serum can be added to the culture, and various cell factors known to be effective in the proliferation or differentiation of such cells can also be added. Examples of such cell factors can include FGF, BMP, and the like.

From the perspective of gas exchange and nutrient supply to the cell masses, and from the perspective of being able to perform all steps in vitro without contact/contamination with other animal cells, the culture within the support carrier is preferably an organ culture. In an organ culture, the culture is generally carried out by floating a porous membrane on a medium suitable for animal cell growth and then placing the support carrier including the first and second cell masses on the membrane. The porous membrane used herein preferably has many pores of about 0.3 to 5 µm, and mention may be made of, for example, Cell Culture Insert (product name) and Isopore Filter (product name).

After constructing the regenerative organ germ from the epithelial cells and mesenchymal cells as described above, a guide is inserted into the regenerative organ germ.

The "guide" used in the present invention is not particularly limited as long as it can be inserted into a regenerative organ germ during culture constructed from an organ culture and facilitate connection between an epithelial cell-side portion of the regenerative organ germ and the recipient-side epithelial cells after transplantation of the regenerative organ germ. For example, mention may be made of a fiber made from a polymer such as nylon or a synthetic or natural bioabsorbable polymer, a metallic fiber such as stainless steel, a carbon fiber, a chemical fiber such as a glass fiber, and a natural animal or plant fiber, and the like. More specifically, mention may be made of a nylon thread, stainless steel wire, or the like. In particular, when using a guide for the regenerative hair follicle germ, hair derived from a living body can be used as the guide. The guide used in the present invention can take on the form of a hollow thread. The diameter and length of the guide can be appropriately designed depending on the organ which is the target of regeneration. For example, as to a guide used for a regenerative hair follicle germ, the diameter thereof is preferably 5 to 100 µm, and more preferably 20 to 50 µm. Also, as to a guide used for a regenerative hair follicle germ, the length thereof is preferably 1 to 10 mm, and more preferably 4 to 6 mm.

Also, if it is necessary to insert the guide into a recipient-side conduit during transplantation as in the case of a regenerative salivary gland germ, for example, the diameter of the guide is preferably 5 µm to 60 µm, and more preferably 20 µm to 40 µm. Also, the length of the guide is preferably 1 mm to 6 mm, and more preferably 2 mm to 3 mm. Further, the surface of the guide is preferably smooth so that it can be easily inserted into the conduit, and the guide preferably retains a degree of hardness that does not harm the tissue. As such a guide, a monofilament material is preferable over a multifilament material such as a braid.

The guide is inserted from the epithelial cell-side of the cell clump that becomes the regenerative organ germ such that the structure of the cell mass that becomes the regenerative organ germ, particularly the contact surface between the epithelial cells and the mesenchymal cells, is not damaged by the insertion of the guide, and the guide vertically penetrates through the epithelial cell fraction and the mesenchymal cell fraction.

Also, the guide can be inserted into the cell clump that becomes the regenerative organ germ immediately after the start of organ culture, in other words, right after disposing the cell masses of epithelial cells and mesenchymal cells in the medium. Also, since the strength of the epithelial cells of a regenerative hair follicle germ increases due to cell adhesion during organ culture, the penetration of the guide can be increased by using a strong material for the guide (such as a stainless steel wire or the like) and sharpening the tip of the guide and the like, enabling the guide to be inserted 1 to 2 days after the start of culture. The guide is preferably inserted immediately after preparation of the organ germ because at this time a flexible material with low foreign-body reaction on a living body such as a nylon thread can be used.

Also, after inserting the guide into the regenerative organ germ, the regenerative organ germ can be cultured in a state in which the guide has been inserted. The duration of culture after insertion of the guide can be appropriately set depending on the organ which is the target of regeneration. For example, when producing a regenerative hair follicle germ, the culture is preferably carried out for 1 to 4 days, and more preferably 1.5 to 2 days. By culturing for 2 days after insertion of the guide, the adhesion between the guide and the regenerative organ becomes strong, and this helps to prevent any deviations that may occur during transplantation. Also, culturing after the guide has been inserted is preferable because the regenerative organ germ on the epithelial cell-side can be elongated along the guide. This elongation can improve the efficiency and stability of autonomous adhesion between the epithelial cell-side portion of the regenerative organ germ and the epithelial cells of the recipient after transplantation of the regenerative organ germ.

Also, according to another embodiment of the present invention, the regenerative organ germ provided with a guide for transplantation produced by the production method of the present invention can be transplanted to a target site.

The regenerative organ germ for transplantation into which the guide has been inserted can be transplanted to a target site by a method known to those skilled in the art. For example, when transplanting a regenerative hair follicle germ, it can be transplanted by using a hair transplant which utilizes the Shapiro hair transplant technique or the Choi hair transplant device or an implanter which utilizes air pressure or the like. The Shapiro hair transplant technique is a method in which a graft wound is created at the transplant site using a micro scalpel or the like and then the hair transplant is transplanted using tweezers. When applying this kind of hair transplant technique, since the regenerative organ germ for transplantation provided by the present invention has a guide, it is possible to operate without directly touching the regenerative hair follicle germ by picking up the guide, and the operation can be therefore easily performed.

The transplantation depth of the regenerative organ germ can be appropriately modified depending on the organ which is the target of regeneration. For example, when transplanting a regenerative hair follicle germ, the depth is preferably 0.05 to 5 mm, more preferably 0.1 to 1 mm, and most preferably 0.3 to 0.5 mm. In particular, when transplanting a regenerative hair follicle germ into a recipient, it is preferably transplanted into the dermic layer, and more preferably above the boundary surface between the dermal and subdermal tissue at which the hair follicle formation and subsequent hair growth efficiency is excellent. It is also preferable to adjust the transplantation depth so that the top end of the epithelial cell portion of the regenerative hair follicle germ is exposed at the top end of the graft wound because this can increase the continuity with the epithelial cells of the recipient.

Also, for example, when transplanting an organ germ for which it is necessary to insert the guide into a conduit on the recipient side, such as when transplanting a regenerative salivary gland germ, it is preferable to conserve the recipient-side conduit for long because this can prevent the guide from falling out after transplantation. Also, from the perspective of improving the nutrient supply, it is preferable for the transplant site to be near a large vein. In doing so, the transplant site becomes easier to adjust if the recipient-side conduit is conserved for long.

Also, after transplantation of the regenerative organ germ, the guide can be fixed to the target site of transplantation using a tape or band for skin-bonding, a suture, and the like so that the guide does not fall out.

After the continuity between the recipient-side epithelial cells and the epithelial cell-derived side of the regenerative organ germ has been secured some time after transplantation of the regenerative organ germ, the guide can be removed from the transplant site. The timing for removal of the guide can be appropriately set depending on the regenerative organ germ. For example, when transplanting a regenerative hair follicle germ, the guide is preferably removed from the transplant site 3 to 7 days after transplant. The guide can also be left so that it naturally falls out from the transplant site. A guide of a bioabsorbable material can be left to naturally fall out from the transplant site or until it decomposes or is absorbed. In particular, when the guide is embedded under the skin of the recipient together with the regenerative organ germ after transplantation, such as in the case of a regenerative salivary gland germ, it is preferable to use a bioabsorbable guide.

In this way, by equipping the regenerative organ germ for transplantation with a guide, the epithelial cell-derived cells of the regenerative organ germ elongate along the guide. Thereby, the continuity between the recipient-side epithelial cells and the epithelial cell side of the regenerative organ germ after transplantation can be improved. In particular, when the guide is maintained outside of the epidermis at the transplant site, such as in the case of a hair follicle or sweat gland, the continuity can be further improved because the recipient-side epithelial cells elongate to the inside of the transplant site along the guide so as to eliminate foreign substances. It is also preferable to insert a guide because the maintenance of the polarity of the epithelial cells and the mesenchymal cells can be improved in the regenerative organ germ during culture. Thereby, the efficiency of regenerative organ formation can be increased and the orientation during transplantation can be facilitated. In particular, when using a guide for a regenerative hair follicle germ, the hair follicle formation can be stimulated in an intended direction, while the continuity between the regenerative hair follicle germ and the recipient-side epithelial cells can be secured. As a result, the hair growth efficiency from the regenerative hair follicle germ can be improved and it is possible to control the hair growth direction.

The terms used in the present specification are used to explain the specific embodiments described herein, and are not intended to limit the present invention.

The terms "comprise/include/contain" used in the present specification are intended to mean that the matters as described (members, steps, elements, numbers, etc.) exist except when another understanding thereof is explicit from the context, and such terms do not exclude the existence of other matters (members, steps, elements, numbers, etc.).

Unless a different definition is given, all of the terms used herein (including technical terms and scientific terms) have the same meaning as those widely understood by those skilled in the art in the technical field to which the present invention belongs. Unless a different definition is explicitly given, the terms used herein should be interpreted with a meaning that is consistent with the meaning in the present specification and the related technical field, and they should not be idealized nor interpreted with an excessively formal meaning.

Some of the embodiments of the present invention have been explained referring to schematic diagrams, but the schematic diagrams may be exaggerated in order to clarify the explanation.

The terms "first", "second", and the like are used to express various elements herein, but it is understood that these elements are not limited by such terms. These terms are used only to distinguish one element from another element, and, for example, the element labeled as "first" can be labeled as "second" and similarly, the element labeled as "second" can be labeled as "first" without departing from the scope of the present invention.

The present invention will now be explained in further detail below referring to Examples. However, the present invention can be embodied by various aspects and should not be construed as limited to the examples described herein.

EXAMPLES (I. Production of Regenerative Hair Follicle)
1. Materials and Methods
(1) Experimental Animals Hair follicles were collected from a C57BL/6 mouse (CLEA Japan) and a C57BL/6 6-TgN (act-EGFP) mouse at 7 to 8 weeks of age. Also, skin containing a body hair germ was collected from a C57BL/6 6-TgN (act-EGFP) mouse (SLC) at 18.0 to 18.5 days gestational age. Also, a regenerative hair follicle germ produced by the experimental method described below was transplanted into a Balb/c nu/nu mouse (SLC) at 6 to 8 weeks of age. The animal care and experimentation was conducted under the approval of the Animal Experimentation Ethics Board of Tokyo University of Science in compliance with the related laws, ministerial ordinances, and guidelines.

(2) Hair Papilla Cell Culture

After euthanizing a C57BL/6 EGFP mouse by cervical dislocation, all layers of the buccal skin and the subcutaneous tissue were collected so as not to damage the hair bulbs. After removal of the subcutaneous tissue surrounding the side whiskers, the hair follicles were isolated. A side whisker hair follicle in growth stages I to IV was selected, and the collagen sheath was removed therefrom using a 25G injection needle to expose the hair follicle. The hair bulb was isolated to extract the hair papilla. The extracted hair follicle and hair papilla were preserved in a DMEM medium (DMEM10) containing 10% fetal bovine serum and 1% penicillin-streptomycin solution. The isolated hair papilla was seeded onto a 3.5 cm culture plastic dish (Nippon Becton Dickinson), and primary culture was conducted in an environment of 5% $CO_2$, 37° C., and 95% humidity in DMEM10 containing 10 ng/ml of FGF2 (Wako Pure Chemical Industries, Ltd.). After culturing for 9 days while exchanging the medium on the $4^{th}$ and $8^{th}$ day, the primary cultured hair papilla cells were used. The primary cultured hair papilla cells were washed 3 times with PBS (−), ablated with 10 mM EDTA solution (GIBCO) containing 0.05% trypsin, trypsin-neutralized in DMEM10, sufficiently washed, and then preserved under ice temperature until time for use.

(3) Acquisition of Hair Follicle Bulge Epithelial Cells

From the extracted side whisker tissue, the collagen sheath was removed using a 25G injection needle, and the tissue was subdivided into the bulge region. The bulge region tissue was reacted for four minutes at 37° C. in a solution of Dispase II (Becton Dickinson) having a final concentration of 4.8 U/ml and 100 U/ml Collagenase (Worthington, Lakewood, N.J.). Subsequently, the bulge region tissue was surgically isolated into a bulge region epithelial tissue and a mesenchymal tissue around the bulge using a 25G injection needle. The isolated bulge region epithelial tissue was subjected to a 1-hour enzyme treatment in an incubator with 0.05% Trypsin (Invitrogen, Carlsbad, US), and then passed through a 35 μm pore cell strainer to obtain unified cells. The cultured hair papilla cells obtained in (2) were also collected with 0.05% Trypsin (Invitrogen, Carlsbad, US), and then passed through a 35 μm pore cell strainer to obtain unified cells.

(4) Production of Regenerative Hair Follicle Germ and Organ Culture

A regenerative hair follicle germ was produced by the organ germ method. The detailed procedures were as follows. The unified bulge region cells derived from the bulge region epithelial tissue and the cultured hair papilla cells obtained as described above were individually transferred into 1.5 ml microtubes (Eppendorf) coated with silicone grease, and then collected as precipitates by centrifugation. Supernatant in the culture solution after the centrifugation was completely removed using GELoader Tip 0.5-20 ml (Eppendorf). Next, a collagen gel drop was prepared by dropping 30 ml of Cellmatrix type I-A (Nitta Gelatin, Osaka, Japan) onto a petri dish coated with silicone grease (Dow Corning Toray). Approximately 0.2 ml of the cultured hair papilla cells prepared as described above were injected into the collagen gel drop using a 0.1 to 10 ml pipette tip (Quality Scientific Plastics) to produce a cell aggregate. Next, approximately 0.2 ml of the bulge region epithelial cells prepared as described above were injected into the same gel drop using a 0.1 to 10 ml pipette tip (Quality Scientific Plastics) so as to closely contact the cultured hair papilla cell aggregate, thereby producing a cell aggregate of the cultured hair papilla cells and the bulge region epithelial cells. Further, from the bulge region epithelial cell side of the cell aggregate of the cultured hair papilla cells and the bulge region epithelial cells, a nylon thread with a total length of 5 mm (Matsuda Medical Industry) was inserted while confirming under a stereoscopic microscope so as to vertically penetrate through the contact surface between the cultured hair papilla cell fraction and the bulge region epithelial cell fraction without damaging the structure of the cell aggregate (particularly the contact surface between the epithelial cells and the mesenchymal cells). Subsequently, the gel drop was left to stand for 5 minutes at 37° C. to solidify it, thereby further strengthening the link between the epithelial cells and the mesenchymal cells so as to produce the regenerative hair follicle germ with a guide.

(5) Acquisition of Embryonic Skin Epithelial and Mesenchymal Cells

Dorsal skin was collected from an EGFP mouse embryo at 18.0 to 18.5 days gestational age, and the epithelial layer and dermic layer were separated by performing a dispase treatment under conditions of 1 hour, 4° C., and 55 rpm shaking based on a partial modification of the method reported by Nakao et al. (Nakao K et al., Nat. Methods, 4(3), 227-30, 2007). The dermic layer was further subjected to two treatments with 100 units/ml collagenase I for 40 minutes at 37° C., and then subjected to unification treatment to obtain the mesenchymal cells. The epithelial layer was also subjected to two treatments with 100 units/ml collagenase I for 40 minutes at 37° C., and then the mesenchymal cells mixed therein were removed, followed by treatment for 10 minutes at 37° C. in a 0.25% trypsin solution containing 100 units/ml collagenase I and then a unification treatment to obtain the epithelial cells.

Also, a cell aggregate of the embryonic skin mesenchymal cells and embryonic skin epithelial cells provided with a guide was produced by a method similar to that described in (4) above, in which the embryonic skin mesenchymal cells were injected into the collagen gel drop instead of the cultured hair papilla cells and then the embryonic skin epithelial cells were injected into the collagen gel drop instead of the bulge region cells so as to closely contact the embryonic skin mesenchymal cell clump.

The cell aggregate of the epithelial cells and the mesenchymal cells produced in the gel was transferred together with the collagen gel onto a 0.4 ml pore size Cell Culture Insert (Becton Dickinson) in which a 6-well plate (Becton Dickinson) to which 1 ml of DMEM10 was added had been set, and then was subjected to the organ culture for 2 days under conditions of 37° C., 5% $CO_2$, and 95% humidity to produce a regenerative hair follicle germ.

(6) Transplantation of Regenerative Hair Follicle Germ into Nude Mouse Skin

The regenerative hair follicle germ produced from the embryonic skin epithelial cells and the embryonic skin mesenchymal cells, and the regenerative hair follicle germ produced from the bulge region epithelial cells and the cultured hair papilla cells derived from an adult whisker were transplanted into the skin of a nude mouse as described below.

A nude mouse was anesthetized with pentobarbital in accordance with a conventional method, and it was placed in a natural recumbent position after disinfecting its back with isodine. The mouse was punctured using a V-lance micro scalpel (Alcon Japan) to form a graft wound from the skin epidermal layer to the lower layer portion of the dermic layer. The graft wound extended from the body surface to a depth of about 400 μm in the vertical direction and about 1 mm in the horizontal direction. The collagen gel was removed from the regenerative hair follicle germ into which a guide made of nylon thread (corresponding to 8-0 nylon suture thread, about 5 mm in length) was inserted, and the regenerative hair follicle germ was inserted using acuminate tweezers No. 5 (Natsume Seisakusho) so that the epithelial cell component was facing the body surface side of the graft wound. The transplant depth was adjusted so that the top end of the epithelial cell component of the regenerative hair follicle germ was exposed at the top end of the graft wound, and the regenerative hair follicle germ was positioned so that the nylon thread guide was exposed at the body surface. The nylon thread guide was fixed with a Steritest strip (3M) to the skin surface near the graft wound, and then the graft wound was protected with Nurseban and Surgical Tape (3M). The protective tape was removed 5 to 7 days after transplantation, and the nylon thread guide was left in the transplant site. When the nylon thread guide remained after one more day, it was removed. The engraftment of the transplant was determined visually or under a fluorescence stereomicroscope, and then the transplant site was observed over time.

(7) Hair Growth Observation Over Time and Histological Analysis

The transplant site of the regenerative hair follicle germ was observed visually and under a fluorescence stereomicroscope to evaluate the hair growth. After the hair began to grow, hair growth and regression was evaluated via periodic photography. Extracted tissue was fixed with Mildform 10N (Wako Pure Chemicals) and then a block was made by embedding in paraffin or freezing in accordance with a conventional method. Serial sections were prepared and subjected to HE staining or Hoechst fluorescent nuclear staining for histological analysis.

2. Results (1) Hair Growth By Intracutaneous Transplant of Regenerative Hair Follicle Germ In order to analyze the transplant location of a regenerated hair follicle germ that was intracutaneously transplanted, a regenerative hair follicle germ was prepared from skin cells of a mouse at 18.5 days gestational age and then transplanted into the skin of a nude mouse. The skin was extracted after transplantation, and a paraffin section thereof was prepared and HE stained. As a result, the transplant location was determined to be within the skin dermic layer and the transplant depth was determined on average to be 393 μm from the body surface. The results immediately after transplant, 3 days after transplant, and 10 days after transplant are shown in FIG. 2. As shown in FIG. 2, when the regenerative hair follicle germ was transplanted into the skin, the guide was fixed in a state in which it was protruding from the body surface (the photo in the upper row of Day 0; the arrow indicates the guide). Also, during the transplant, the regenerative hair follicle germ and the recipient epithelium were not connected (the photo of the HE-stained section in the lower row of Day 0 in FIG. 2). By the $3^{rd}$ day after transplant, the epithelial component of the regenerative hair follicle germ and the recipient skin epidermal layer were connected via the guide (the photo of the HE-stained section in the lower row of Day 3 in FIG. 2; the arrow indicates the connected portion). By the $10^{th}$ day after transplant, the hair follicle was regenerated, and regenerative hair began to grow from the body surface on the $14^{th}$ day on average (Day 10 in FIG. 2) with a hair growth frequency of 90%.

Also, the results upon transplanting a regenerative hair follicle germ derived from an adult side whisker into the back of a nude mouse so that the transplant depth was the same as described above are shown in FIG. 4. FIG. 4A is a photo depicting the insertion of the guide into the regenerative hair follicle germ. "E" indicates the portion derived from the bulge region epithelial cells, "DP" indicates the portion derived from the cultured hair papilla cells, and "G" indicates the guide. FIG. 4B shows a photo that tracks the transplant site with a fluorescence stereomicroscope. After transplanting the adult whisker-derived regenerative hair follicle germ, regenerative hair began to grow from the body surface 21 days on average after transplantation (FIG. 4C) with a hair growth frequency of 74%.

(2) Tissue Analysis of Regenerative Hair Follicle

A regenerated hair follicle was extracted and carried out for tissue analysis. The results thereof are shown in FIG. 5. Enlarged versions of the portions within the square boxes in the low magnification microscope images on the left are shown in the photos in the middle and right columns. The regenerative hair follicle was distinguished from the surrounding nude mouse hair follicles using GFP fluorescence (the lower left-hand photo in FIG. 5). The epithelial tissue of the regenerated hair follicle was connected to the recipient skin epidermal layer, and the recipient-derived cells were dominant in the epidermal basal layer of the connected portion. Also, in the enlarged photos of the top portion of the regenerative hair, regeneration of the sebaceous glands was confirmed (the portion marked with the arrow in the top and bottom photos in the center column in FIG. 5). Sebaceous glands derived from the regenerative hair follicle germ were mixed with those derived from the recipient cells, but the sebaceous glands below those of the regenerative hair follicle were derived from the transplanted regenerative hair follicle germ. Further, the photos on the right side in FIG. 5 show hair bulbs. In the lower right-hand photo, since GFP fluorescence in the hair (dermal) papilla (DP) site was confirmed, it was demonstrated that the hair papilla was derived from the transplanted regenerative hair follicle germ. In this way, the regenerative hair follicle exhibited a histologically normal hair follicle structure, and the regenerative hair follicle derived from an adult side whisker was clearly larger than the body hair.

(3) Analysis of Regenerative Hair Shaft

The regenerative hair derived from an embryonic body hair was 100% black hair, and the regenerative hair derived from an adult side whisker was 95.5% white hair. FIG. 6 shows photos depicting observation by an optical microscope and a scanning electron microscope. A spiral medulla of hair shaft (M) that is characteristic of whisker-like hard hair was observed inside the dashed lines (FIG. 6a), and a cuticle structure equivalent to a normal side whisker was confirmed (FIG. 6b). In this way, the regenerative whisker exhibited a medulla of hair shaft and a cortex equivalent to those of natural hair, and also presented a clear whisker-like structure.

(4) Hair Cycle of Regenerative Hair

Upon tracking the growth and regression of the hair shaft of the regenerative whisker, the hair shaft regressed as the hair cycle progressed, and then a new hair shaft grew from the pore site at which the hair fell out (FIG. 7). Also, the duration of the hair cycle was equivalent to that of the hair cycle of a natural whisker and no significant difference was observed (FIG. 8). From such results, it was clear that the regenerative hair retained its connection with the recipient epidermal layer to repeat hair growth and regression, even if it passes through the hair cycle.

(II. Production of Regenerative Salivary Gland)

(1) Production of Regenerative Salivary Gland Germ and Organ Culture

A salivary gland germ was produced using the organ germ method for the purpose of regeneration of a salivary gland.

A submandibular gland germ was surgically extracted from a C57BL/6 mouse fetus at 13.5 to 14.5 days gestational age. The extracted submandibular gland germ was reacted for 1.5 minutes at 25° C. in a solution of Dispase II (Becton Dickinson) having a final concentration of 50 U/ml. Subsequently, the submandibular gland germ was isolated into a submandibular gland epithelial tissue and a submandibular gland mesenchymal tissue using a 25G injection needle. Further, the mesenchymal tissue was subjected to a 10-minute enzyme treatment in a 37° C. warm bath with a solution of Collagenase having a final concentration of 50 U/ml (Worthington, Lakewood, N.J.) and a solution of Trypsin (Invitrogen, Carlsbad, US) having a final concentration of 0.25%, and then passed through a 22 μm pore cell strainer to obtain completely unified mesenchymal cells. The epithelial tissue was subjected to two 15-minute enzyme treatments in a 37° C. warm bath with a solution of Collagenase having a final concentration of 100 U/ml (Worthington, Lakewood, N.J.), followed by a 5-minute enzyme treatment in a 37° C. warm bath with a solution of Trypsin (Invitrogen, Carlsbad, US) having a final concentration of 0.25%, and then passed through a 22 μm pore cell strainer to obtain completely unified epithelial cells.

Using the obtained epithelial cells and mesenchymal cells, a regenerative salivary gland germ was produced in a collagen gel by the organ germ method (FIG. 9). The detailed procedures were as follows. The unified epithelial cells and the unified mesenchymal cells obtained as described above were individually transferred into 1.5 ml microtubes (Eppendorf) coated with silicone grease, and then centrifuged. Supernatant in the culture solution after the centrifugation was completely removed using GELoader Tip 0.5-20 ml (Eppendorf), and the unified epithelial cells and the unified mesenchymal cells were respectively collected as precipitates. Next, a collagen gel drop was prepared by dropping 30 μl of Cellmatrix type I-A (Nitta Gelatin, Osaka, Japan) onto a petri dish coated with silicone grease (Dow Corning Toray). Approximately 0.3 μl of the unified mesenchymal cells prepared as described above were injected into the collagen gel drop using a 0.1 to 10 ml pipette tip (Quality Scientific Plastics) to produce a cell aggregate. Next, approximately 0.2 μl of the unified epithelial cells prepared as described above were injected into the same gel drop using a 0.1 to 10 ml pipette tip (Quality Scientific Plastics) so as to closely contact the mesenchymal cell aggregate, thereby producing a cell aggregate of the submandibular gland germ-derived epithelial cells and mesenchymal cells.

The cell aggregate of the submandibular gland germ-derived epithelial cells and mesenchymal cells produced in the gel was transferred together with the collagen gel onto a 0.4 ml pore size Cell Culture Insert (Becton Dickinson) in which a 6-well plate (Becton Dickinson) to which 1 ml of DMEM10 was added had been set, and then was subjected to the organ culture under conditions of 37° C., 5% $CO_2$, and 95% humidity to produce a regenerative salivary gland germ.

During the organ culture of the regenerative salivary gland germ, it was observed that the epithelial cells began to invaginate into the mesenchymal cell side 24 hours after the start of culture (FIG. 10). The top two rows of photos in FIG. 10 illustrate the state at several elapsed times when a submandibular gland extracted from an embryonic mouse was organ cultured as is after extraction, and the bottom two rows of photos in FIG. 10 illustrate the state at several elapsed times when a regenerative salivary gland germ constructed by the organ germ method was organ cultured. Upon analysis by hematoxylin-eosin staining (HE staining), it was confirmed that the tips of the invaginated epithelial tissue were branched 72 hours after the start of culture (FIG. 10).

From the above results, it was demonstrated that a regenerative salivary gland germ could be produced using the organ germ method.

As shown in FIG. 9, submandibular gland primordia at different stages of development were obtained from a mouse embryo at a gestational age of 13.5 days (refer to the photos of early, mid, and late stage in FIG. 9). However, a regenerative salivary gland germ reconstructed from epithelial cells and mesenchymal cells was able to be produced by the above-described method from the submandibular gland primordia at every stage of development.

(2) Production of Regenerative Salivary Gland Germ with Guide Thread

A bioabsorbable thread (Gunze Co.) with a total length of 3 mm was inserted from the epithelial cell side into the regenerative salivary gland germ produced by the method described in (1) above, while confirming under a stereoscopic microscope, so as to vertically penetrate through the contact surface between the epithelial cell portion and the mesenchymal cell portion without damaging the structure of the regenerative salivary gland germ (particularly the contact surface between the epithelial cells and the mesenchymal cells). After the insertion of the guide, the regenerative salivary gland germ was subjected to the organ culture for 60 hours.

As a result, it was observed that after about 24 hours had elapsed from the start of the organ culture, the epithelial cell side of the regenerative salivary gland germ began to move/elongate along the guide thread, and after 60 hours from the start of culture, a conduit-like structure was exhibited (FIG. 11; the arrows in the photos in the bottommost row indicate the conduit-like structure).

(3) Transplantation of Regenerative Salivary Gland Germ to Parotid Gland Conduit Portion The acinar portion of a parotid gland of an adult mouse was surgically removed to expose the conduit portion connected to the parotid gland. Next, the regenerative salivary gland germ with a guide produced by the method described in (2) above and subjected to the organ culture for two days was transplanted to the parotid gland conduit portion together with the collagen gel. During the transplantation, the position of the guide thread was adjusted so that the cut surface of the conduit and the epithelial tissue of the regenerative salivary gland germ were proximal to each other, and the guide was inserted into the recipient-side parotid gland conduit. Also, the collagen gel including the regenerative salivary gland germ and the masseter were sutured together with 8-0 nylon suture thread (Bear Medic, Chiba, Japan) so that the transplanted regenerative salivary gland germ would not move (FIG. 12).

The regenerative salivary gland germ was histologically evaluated by HE staining 30 days after transplant. From the HE stained images, conduit cells and serous acinar cell-like cells similar to those in a natural submandibular gland were confirmed in the regenerative salivary gland germ (FIG. 13; the arrows in the photos in the bottom row in FIG. 13 indicate serous acinar cell-like cells).

In this way, a salivary gland was able to be reconstructed by the regenerative organ germ method. It was also possible to reconstruct a submandibular gland even from a regenerative salivary gland germ derived from a submandibular gland at a parotid gland site, which is another salivary gland.

(4) Evaluation of Salivary Secretory Pathway of Regenerative Salivary Gland

For the purpose of clarifying that the submandibular gland-derived regenerative salivary gland germ and the adult mouse parotid gland conduit were connected and the salivary secretory pathway was being retained, on the $30^{th}$ day after transplant of the regenerative salivary gland germ, the transplant site and the parotid gland conduit were exposed by a surgical method, and an Evans blue solution was injected by microinjection towards the regenerative salivary gland germ from the conduit more toward the oral cavity side than the transplant site of the regenerative salivary gland germ.

As a result, under observation with a stereoscopic microscope, it was observed that the injected Evans blue solution flowed through the parotid gland conduit to the transplanted regenerative salivary gland germ (FIG. 14). This suggests that the regenerative salivary gland and the parotid gland conduit were connected and the salivary secretory pathway was being retained.

Upon comparing transitions in weight and survival rate between a salivary gland-deficient mouse from which all of the salivary glands were removed and a mouse from which all of the salivary glands were removed and then a regenerative salivary gland germ with a guide was transplanted to a submandibular gland site (the transplant mouse), the salivary gland-deficient mouse continued to lose weight on each day that was tracked after the day of salivary gland removal, whereas the weight of the transplant mouse gradually recovered from the about the $3^{rd}$ or $4^{th}$ day after transplantation and recovered to a nearly normal weight on about the $6^{th}$ day (FIG. 15). Also, the survival rate of the salivary gland-deficient mouse was 20% or less from the $4^{th}$ day and beyond after the day of salivary gland removal, whereas the survival rate of the transplant mouse was about 70% from the $4^{th}$ day and beyond after the day of transplant (FIG. 15).

(III. Production of Regenerative Lacrimal Gland)
(1) Production of Regenerative Lacrimal Gland Germ and Organ Culture A regenerative lacrimal gland germ was produced using the organ germ method for the purpose of regeneration of a lacrimal gland as follows.

A lacrimal gland germ was surgically extracted from a C57BL/6 mouse fetus at 16.5 to 17.5 days gestational age. The extracted lacrimal gland germ was reacted for 1.5 minutes at 25° C. in a solution of Dispase II (Becton Dickinson) having a final concentration of 50 U/ml. Subsequently, the lacrimal gland germ was isolated into a lacrimal gland epithelial tissue and a lacrimal gland mesenchymal tissue using a 25G injection needle. Further, the mesenchymal tissue was subjected to a 10-minute enzyme treatment in a 37° C. warm bath with a solution of Collagenase having a final concentration of 50 U/ml (Worthington, Lakewood, N.J.) and a solution of Trypsin (Invitrogen, Carlsbad, US) having a final concentration of 0.25%, and then passed through a 22 μm pore cell strainer to obtain completely unified mesenchymal cells. The epithelial tissue was subjected to two 15-minute enzyme treatments in a 37° C. warm bath with a solution of Collagenase having a final concentration of 100 U/ml (Worthington, Lakewood, N.J.), followed by a 5-minute enzyme treatment in a 37° C. warm bath with a solution of Trypsin (Invitrogen, Carlsbad, US) having a final concentration of 0.25%, and then passed through a 22 μm pore cell strainer to obtain completely unified epithelial cells.

Using the obtained epithelial cells and mesenchymal cells, a regenerative lacrimal gland germ was produced in a collagen gel by the organ germ method. The detailed procedures were as follows. The unified epithelial cells and the unified mesenchymal cells obtained as described above were individually transferred into 1.5 ml microtubes (Eppendorf) coated with silicone grease, and then centrifuged. Supernatant in the culture solution after the centrifugation was completely removed using GELoader Tip 0.5-20 ml (Eppendorf), and the unified epithelial cells and the unified mesenchymal cells were respectively collected as precipitates. Next, a collagen gel drop was prepared by dropping 30 μl of Cellmatrix type I-A (Nitta Gelatin, Osaka, Japan) onto a petri dish coated with silicone grease (Dow Corning Toray).

Approximately 0.3 μl of the unified mesenchymal cells prepared as described above were injected into the collagen gel drop using a 0.1 to 10 ml pipette tip (Quality Scientific Plastics) to produce a cell aggregate. Next, approximately 0.2 μl of the unified epithelial cells prepared as described above were injected into the same gel drop using a 0.1 to 10 ml pipette tip (Quality Scientific Plastics) so as to closely contact the mesenchymal cell aggregate, thereby producing a cell aggregate of the lacrimal gland germ-derived epithelial cells and mesenchymal cells (FIG. 16).

The cell aggregate of the lacrimal gland germ-derived epithelial cells and the lacrimal gland germ-derived mesenchymal cells produced in the gel was transferred together with the collagen gel onto a 0.4 ml pore size Cell Culture Insert (Becton Dickinson) in which a 6-well plate (Becton Dickinson) to which 1 ml of DMEM10 was added had been set, and then was subjected to the organ culture under conditions of 37° C., 5% $CO_2$, and 95% humidity to produce a regenerative lacrimal gland germ.

During the organ culture of the regenerative lacrimal gland germ, it was observed that the epithelial cells began to invaginate into the mesenchymal cell side 24 hours after the start of culture similar to the lacrimal gland germ extracted from the fetus (FIG. 17). From such result, it was demonstrated that a regenerative lacrimal gland can be produced using the organ germ method.

(2) Production of Regenerative Lacrimal Gland with Guide and Transplantation

A bioabsorbable thread (Gunze Co.) with a total length of 3 mm was inserted from the epithelial cell side into the regenerative lacrimal gland germ produced by the method described in (1) above, while confirming under a stereoscopic microscope, so as to vertically penetrate through the contact surface between the epithelial cell portion and the mesenchymal cell portion without damaging the structure of the regenerative lacrimal gland germ (particularly the contact surface between the epithelial cells and the mesenchymal cells). After insertion of the guide, the regenerative lacrimal gland germ was subjected to the organ culture for 2 days.

After performing the organ culture, the acinar portion of the lacrimal gland of an adult mouse was removed to expose the conduit portion, and the regenerative lacrimal gland germ was transplanted to the lacrimal gland conduit using the same method as in the case of transplanting a regenerative salivary gland germ.

As a result, upon confirming the regenerative lacrimal gland germ 20 days after the transplant, it was confirmed that it had adhered at the transplant site and had grown significantly (FIG. 18). Also, it was visually confirmed that the regenerative lacrimal gland germ was connected to the natural lacrimal gland conduit.

As explained in detail above, the regenerative organ germ provided with a guide according to the invention of the present application connected reliably to the recipient-side epithelial cells and became a functional regenerative organ after the transplant. In particular, in the regenerative hair follicle germ, it was clear that hair growth from the body surface occurs at a high frequency. The regenerative hair follicle retained continuity via the pore portion with the recipient epidermal layer throughout the hair cycle, and repeated hair growth at the same location was observed. Also, the transplantation technique of a regenerative hair follicle germ with a guide was very simple and widely applicable. Also, in a regenerative organ having a conduit, the epithelial cell-derived portion of the regenerative organ germ and the recipient-side conduit could be stably connected to each other after the transplantation into the recipient, and it was clear that the organ function via the conduit could be exhibited.

By providing the above-described effects, the regenerative organ germ for transplantation produced by the present invention can provide novel organ replacement and regenerative medical techniques which can be widely applied in the field of medical industry.

The invention claimed is:

1. A method for producing a regenerative hair follicle germ having a guide for transplantation, comprising:
    preparing a regenerative hair follicle germ by closely contacting a first cell mass substantially consisting of mesenchymal cells and a second cell mass substantially consisting of epithelial cells and culturing the first cell mass and the second cell mass within a gel or liquid support carrier that is made of collagen, agarose gel, carboxymethyl cellulose, gelatin, agar, hydrogel, elastin, fibrin, or laminin;
    inserting the guide into the regenerative hair follicle germ,
        wherein the guide is maintained in a state in which the guide protrudes from the regenerative hair follicle germ before implantation,
        wherein the guide is consisting essentially of a fiber selected from the group consisting of a fiber made from a polymer, a metallic fiber, a carbon fiber, a chemical fiber, and a natural animal or plant fiber, and
        wherein a part of the guide is surrounded by the regenerative hair follicle germ; and
    culturing the regenerative hair follicle germ before implantation.

2. The method according to claim 1, wherein the culturing of the regenerative hair follicle germ is conducted for a period of several days after inserting the guide.

3. The method according to claim 1, wherein at least one of the first cell mass and the second cell mass is derived from an organ to be regenerated.

4. The method according to claim 1, wherein the first cell mass and the second cell mass are both derived from an organ to be regenerated.

5. The method according to claim 1, wherein the epithelial cells are bulge region epithelial cells or hair matrix basal epithelial cells.

6. The method according to claim 1, wherein the mesenchymal cells are hair papilla cells or dermal root sheath cells.

7. The method according to claim 1, wherein the guide is a chemical fiber.

8. The method according to claim 1, wherein the guide is bioabsorbable.

9. The method according to claim 1, wherein the guide is a nylon thread.

10. The method according to claim 2, wherein at least one of the first cell mass and the second cell mass is derived from an organ to be regenerated.

11. The method according to claim 2, wherein the first cell mass and the second cell mass are both derived from an organ to be regenerated.

12. The method according to claim 1, wherein the guide has a diameter from 5 μm to 100 μm.

13. The method according to claim 1, the method further comprising removing the regenerative hair follicle germ from the support carrier before implantation.

14. The method according to claim 1, wherein the guide is inserted from the epithelial cell-side of the first and second cell masses such that the guide penetrates through a fraction of the epithelial cells and a fraction of the mesenchymal cells.

* * * * *